US012083500B2

(12) United States Patent
Adachi

(10) Patent No.: US 12,083,500 B2
(45) Date of Patent: Sep. 10, 2024

(54) SEPARATION MEDIUM, USE FOR SEPARATION MEDIUM, STEVIOL GLYCOSIDE SEPARATION METHOD USING SEPARATION MEDIUM, AND STEVIOL GLYCOSIDE PRODUCTION METHOD USING SEPARATION METHOD

(71) Applicant: Mitsubishi Chemical Corporation, Tokyo (JP)

(72) Inventor: Tadashi Adachi, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 382 days.

(21) Appl. No.: 17/230,082

(22) Filed: Apr. 14, 2021

(65) Prior Publication Data

US 2021/0229071 A1    Jul. 29, 2021

Related U.S. Application Data

(60) Division of application No. 16/538,875, filed on Aug. 13, 2019, now abandoned, which is a continuation of application No. PCT/JP2018/006320, filed on Feb. 21, 2018.

(30) Foreign Application Priority Data

Feb. 22, 2017  (JP) ................ 2017-031392

(51) Int. Cl.
| | |
|---|---|
| *B01J 20/285* | (2006.01) |
| *A23L 27/30* | (2016.01) |
| *B01D 15/42* | (2006.01) |
| *B01J 20/26* | (2006.01) |
| *B01J 20/28* | (2006.01) |
| *C07J 17/00* | (2006.01) |

(52) U.S. Cl.
CPC ............ *B01J 20/285* (2013.01); *A23L 27/36* (2016.08); *B01D 15/424* (2013.01); *B01J 20/262* (2013.01); *B01J 20/267* (2013.01); *B01J 20/28016* (2013.01); *B01J 20/2808* (2013.01); *B01J 20/28083* (2013.01); *B01J 20/28085* (2013.01); *C07J 17/005* (2013.01); *A23V 2002/00* (2013.01); *B01J 2220/52* (2013.01)

(58) Field of Classification Search
CPC .......... A61K 31/704; C07H 1/06; C07H 1/08; C07H 15/24; C07H 15/256
See application file for complete search history.

(56) References Cited

U.S. PATENT DOCUMENTS

| 4,772,635 A * | 9/1988 | Mitschker .............. B01J 20/267 |
| | | 525/379 |
| 5,190,660 A | 3/1993 | Lindoy et al. |
| 6,260,715 B1 * | 7/2001 | Simard .............. B01D 67/0093 |
| | | 427/245 |
| 2008/0203029 A1 | 8/2008 | Deorkar et al. |
| 2011/0183056 A1 | 7/2011 | Morita et al. |
| 2014/0187761 A1 | 7/2014 | Morita et al. |
| 2014/0194543 A1 | 7/2014 | Deorkar et al. |
| 2016/0058050 A1 | 3/2016 | Morita et al. |
| 2018/0077959 A1 | 3/2018 | Morita et al. |
| 2019/0357581 A1 | 11/2019 | Morita et al. |
| 2021/0037864 A1 | 2/2021 | Morita et al. |

FOREIGN PATENT DOCUMENTS

| CN | 102060891 A | 5/2011 |
| CN | 102216313 A | 10/2011 |
| CN | 102603984 A | 7/2012 |
| CN | 104098734 A | 10/2014 |
| CN | 105440197 A | 3/2016 |
| JP | 60-160823 A | 8/1985 |
| JP | 2-251251 A | 10/1990 |
| JP | 5-86205 A | 4/1993 |
| JP | 5-86206 A | 4/1993 |
| JP | 2008-528966 A | 7/2008 |
| JP | 2012-504552 A | 2/2012 |
| JP | 2017-211352 A | 11/2017 |

OTHER PUBLICATIONS

Lv, X. et al "Preparative separation of steviol gycosides . . . " Acta Chromatog., vol. 26, pp. 123-135. (Year: 2014).*
Shi, Y. et al "An efficient for decoloration of polysaccharides . . . " Food Chem., vol. 217, pp. 461-467. (Year: 2017).*
International Search Report issued May 29, 2018 in PCT/JP2018/006320 filed Feb. 21, 2018 (with English translation).
Written Opinion issued May 29, 2018 in PCT/JP2018/006320 filed Feb. 21, 2018.
General columns catalog Shodex 2016-2017, Showa Denko Kabushiki Kaisha, 2016, pp. 22-23.
Diaion Manual 2 (Mitsubishi Chemical Corporation), 2016, pp. 302-305.
Zhang, R. et al., Hydrophilic modification gigaporous resins with poly (ethylenimine) for high-throughput proteins ion-exchange chromatography, Journal of Chromatography A, 2014, vol. 1343, pp. 109-118.
Zhou, W. et al., Synthesis of macroporous poly (glycidyl methacrylate) microspheres by surfactant reverse micelles swelling method, European Polymer Journal, 2007, vol. 43, pp. 4493-4502.
Ba, Jing et al., Separation of Rebaudiana A from Steviol glycoside using a polymeric adsorbent with multi-hydrogen bonding in a non-aqueous system, Journal of Chromatography B, 2014, vol. 971, pp. 141-149.

(Continued)

*Primary Examiner* — Leigh C Maier
(74) *Attorney, Agent, or Firm* — Oblon, McClelland, Maier & Neustadt, L.L.P.

(57) ABSTRACT

An object of the present invention is to provide a separation medium and a separation method, ensuring high selectivity and good separation efficiency for specific steviol glycosides. The present invention is related to a separation medium in which polyethyleneimine is immobilized to porous particles of a (meth)acrylic polymer having a crosslinked structure and a hydroxyl group.

20 Claims, 10 Drawing Sheets

(56) References Cited

OTHER PUBLICATIONS

Yu, Y., et al., "Preparation of Mixed-mode Chromatography Supports Based on Gigaporous Polymer Microspheres", Chin. J. Anal. Chem., vol. 44, No. 12, pp. 1874-1879 (2016).

Chen, B. et al., Purification and Preparation of Rebaudioside A from Steviol Glycosides Using One-Dimensional Hydrophilic Interaction Chromatography, Journal of Chromatographic Science, 2016, vol. 54, No. 8, pp. 1408-1414.

Combined Chinese Office Action and Search Report issued Apr. 8, 2022 in Patent Application No. 201880011416.X (with English machine translation and English translation of Category of Cited Documents), 23 pages.

Chinese Offices Action issued on Dec. 26, 2023 in Chinese Patent Application 201880011416.X, (with English translation) 27 pages.

Combined Chinese Office Action and Search Report issued Aug. 19, 2022, in corresponding Chinese Patent Application No. 201880011416.X (with English Translation), 23 pages.

Biotechnology, Malu, Morta Morta, Shanghai Wadade Academy Press, pp. 202-203. Dec. 31, 1991, (with English Translation).

"Application of Capillary Electrophoresis in Pharmaceutical Analysis", Lewis, Sieam Northw., pp. 55-57. Oct. 31, 2013, (with English Translation).

Japanese Office Action issued Jul. 6, 2021 in Japanese Patent Application No. 2019-501390 (with unedited computer generated English translation), 5 pages.

Combined Chinese Office Action and Search Report issued Sep. 30, 2021 in Patent Application No. 201880011416.X (with English language translation), 23 pages.

\* cited by examiner

SEPARATION MEDIUM, USE FOR SEPARATION MEDIUM, STEVIOL GLYCOSIDE SEPARATION METHOD USING SEPARATION MEDIUM, AND STEVIOL GLYCOSIDE PRODUCTION METHOD USING SEPARATION METHOD

CROSS REFERENCE TO RELATED APPLICATIONS

This application is a divisional application of U.S. patent application Ser. No. 16/538,875, filed on Aug. 13, 2019, abandoned, which is a National Stage of PCT/JP2018/006320 filed Feb. 21, 2018. This application also claims the benefit of JP 2017-031392 filed Feb. 22, 2017. The entire disclosures of these related applications are incorporated herein by reference.

TECHNICAL FIELD

The present invention relates to a separation medium suitably used in a packing material for chromatography, among others, a separation medium having high selectivity for a specific steviol glycoside, and also relates to use of the separation medium, a steviol glycoside separation method using the separation medium, and a steviol glycoside production method using the separation method.

BACKGROUND ART

Steviol glycosides are contained in stevia leaf, etc. Since steviol glycosides are low-caloric and have several score times to several hundred times of the sweetness of sucrose, demands therefor as a diet sweetener are growing. With respect to a method for separating and purifying steviol glycosides from stevia leaves, a method of extracting the stevia leaf with water, a water-soluble organic solvent or a mixed solvent thereof and after precipitation and filteration/removal of various foreign substances by a chemical treatment, performing separation, demineralization and decolorization by using various separation media such as synthetic adsorbent or ion-exchange resin is frequently used (see, for example, Non-Patent Literature 1).

In the stevia leaf, although various steviol glycosides having various chemical structures are present, a main component includes stevioside and rebaudioside A. Stevioside is most abundantly contained in the normal stevia leaf but has a unique flavor, in addition to sweetness, and this is supposed to be disadvantageous in applications as a sweetener for a wide range of uses. On the other hand, rebaudioside A has little unique flavor, in comparison with stevioside, and therefore, supply of high-purity rebaudioside A is being demanded.

As the method for obtaining high-purity rebaudioside A, for example, the method described in Patent Literature 1 of using a stevia leaf variety having high rebaudioside A content and content rate is an easiest method, but such a variety cannot be used in general. Accordingly, a method for separating and purifying high-purity rebaudioside A from an extract of a normal stevia leaf variety containing various steviol glycosides is required.

For example, there is a separation and purification method for general steviol glycosides, where, as illustrated in Non-Patent Literature 1, a sweetener component is adsorbed using a synthetic adsorbent, eluted with an aqueous alcohol solution, demineralized and decolorized through two beds and two columns of a cation-exchange resin and an anion-exchange resin, and then subjected to finishing purification. However, in the method, rebaudioside A could not be separated and purified in high purity.

Then, Non-Patent Literature 2 has proposed a separation medium in which a polyalkylenepolyamine having a low molecular weight ranging from ethylenediamine to tetraethylenepentamine is bonded to a crosslinked synthetic polymer particle.

BACKGROUND ART LITERATURE

Patent Literature

Patent Literature 1: JP-A-S60-160823

Non-Patent Literature

Non-Patent Literature 1: DIAION MANUAL 2 (issued by Mitsubishi Chemical Corporation)
Non-Patent Literature 2: Journal of Chromatography B, 971 (2014), p. 141.

SUMMARY OF INVENTION

Technical Problem

However, in a practical example of the separation medium of Non-Patent Literature 2, an expensive n-butyl alcohol solution which has a low water miscibility of 7.8% by mass (20° C.), by which making it cumbersome to transfer the separation medium after the separation step to the water washing and regeneration step, is used in the separation step and therefore, this separation medium is industrially disadvantageous.

In this way, a separation medium and a separation method for favorably separating and purifying a specific steviol glycoside, particularly, high-purity rebaudioside A, from general stevia leaves with high separation property by using a solvent freely miscible with water, which facilitates industrial use, have not yet been known.

The present invention has been made by taking into account such problems, and an object of the present invention is to provide a separation medium having high selectivity for steviol glycosides and ensuring good separation efficiency of, among others, rebaudioside A, and a separation method for steviol glycosides.

Solution to Problem

As a result of intensive studies, the present inventors have found that a separation medium in which polyethyleneimine is immobilized to a specific porous particle exhibits the adsorption and separation performance with high selectivity for a specific steviol glycoside, particularly, for rebaudioside A, and have accomplished the present invention.

More specifically, the gist of the present invention resides in the followings.

[1] A separation medium in which polyethyleneimine is immobilized to porous particles of a (meth)acrylic polymer having a crosslinked structure and a hydroxyl group.

[2] The separation medium according to the above [1], wherein a mass average molecular weight of the polyethyleneimine is 200 or more.

[3] The separation medium according to the above [1] or [2], wherein a nitrogen content rate is from 0.3 to 30% by mass.

[4] The separation medium according to any one of the above [1] to [3], wherein a pore diameter of the porous particles is from 1 to 1,000 nm.

[5] A separation medium used for separation of a steviol glycoside, in which polyethyleneimine is immobilized to at least one porous particles selected from the group consisting of a (meth)acrylic polymer, a vinyl acetate polymer, polysaccharides, silica and glass.

[6] The separation medium according to the above [5], wherein the porous particles contain a (meth)acrylic polymer.

[7] The separation medium according to the above [5] or [6], wherein a nitrogen content rate is from 0.3 to 30% by mass.

[8] Use of the separation medium according to any one of the above [1] to [7] for separation of a steviol glycoside.

[9] A separation method for a steviol glycoside, containing a liquid chromatography step of loading a solution containing two or more types of steviol glycosides to the separation medium according to any one of the above [1] to [7] and allowing a solvent A to flow through the separation medium, thereby separating at least two types of steviol glycosides included in the steviol glycosides.

[10] The separation method for steviol glycosides according to the above [9], wherein the solution containing two or more types of steviol glycosides contain rebaudioside A and at least one fraction obtained in the liquid chromatography step is a fraction containing rebaudioside A as a main component.

[11] The separation method for steviol glycosides according to the above [9] or [10], wherein the solvent A contains alcohols freely miscible with water.

[12] The separation method for steviol glycosides according to any one of the above [9] to [11], wherein in the liquid chromatography step, decolorization of a pigment component in the solution is performed at the same time.

[13] A separation method for a steviol glycoside, containing an adsorption step of bringing a solution containing two or more types of steviol glycosides and a solvent B into contact with the separation medium according to any one of the above [1] to [7] to adsorb the steviol glycosides to the separation medium, and an elution step of eluting the steviol glycosides from the separation medium by using a solvent C, thereby obtaining two or more fractions containing different steviol glycosides as a main component, respectively.

[14] The separation method for a steviol glycoside according to the above [13], wherein the solution containing two or more types of steviol glycosides contains rebaudioside A and at least one fraction obtained in the elution step is a fraction containing rebaudioside A as a main component.

[15] The separation method for steviol glycosides according to the above or [14], wherein the solvent B and the solvent C contain alcohols freely miscible with water.

[16] The separation method for steviol glycosides according to any one of the above to [15], wherein the solvent C is higher in polarity than the solvent B.

[17] The separation method for steviol glycosides according to any one of the above to [16], wherein the solvent B is propyl alcohol, ethyl alcohol or methyl alcohol.

[18] The separation method for steviol glycosides according to any one of the above to [17], wherein in the elution step, decolorization of a pigment component in the solution is performed at the same time.

[19] A production method for steviol glycosides, containing a step of separating at least two types of steviol glycosides from a solution containing two or more types of steviol glycosides by the separation method for a steviol glycoside according to any one of the above [9] to [18].

Effects of Invention

The separation medium of the present invention is a separation medium in which polyethyleneimine is immobilized to a specific porous particle, and based on the configuration, the separation medium exhibits the adsorption and separation performance with high selectivity for a specific steviol glycoside, particularly, for rebaudioside A. In addition, the separation medium can be suitably used in an industrial separation purification step for steviol glycosides, and a separation method capable of separating and purifying the objective steviol glycoside in high purity can be realized.

DESCRIPTION OF EMBODIMENTS

Figure 1:
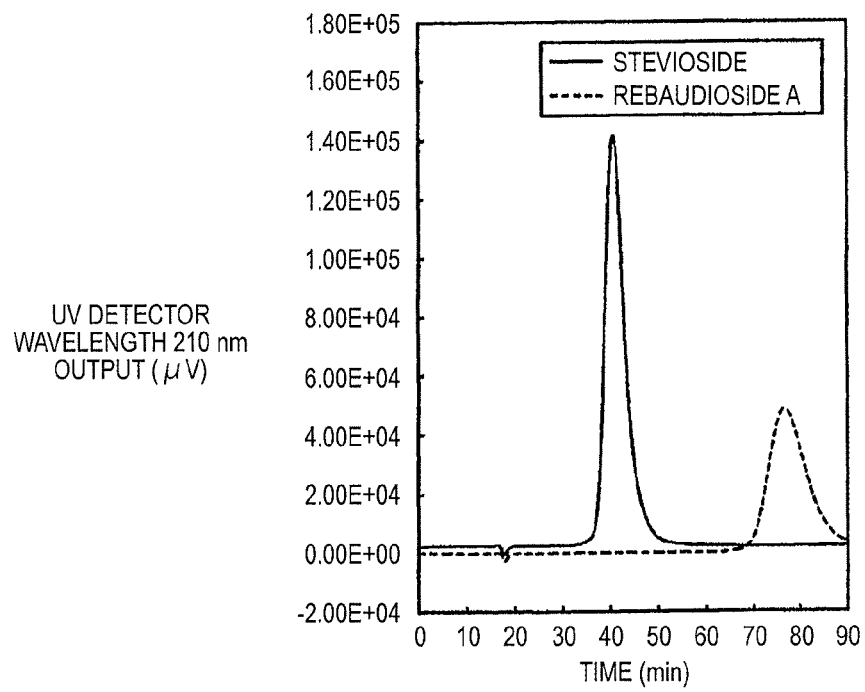
FIG. 1 is a graph illustrating results of performing evaluation of a separation property by chromatography using a separation medium of Example 1.

Although the present invention is described in detail below by referring to illustrative examples, etc., the present invention is not limited to the following illustrative examples and can be implemented by making various changes without departing from the gist of the present invention. Here, in the present description, when values are expressed using "to" therebetween, the expression is used to include the numerical or physical property values before and after "to"

In this connection, in the present description, "(meth) acryl" indicates one or both of "acryl" and "methacryl", and the same holds true for "(meth)acrylate". In addition, "(poly) ethylene . . . " indicates one or both of "ethylene . . . " and "polyethylene . . . ".

[1] Separation Medium

The separation medium of the present invention is characterized in that polyethyleneimine is immobilized to a specific porous particle. In the following, each constituent element is described in detail.

[1-1] Porous Particle

In the present description, the porous particles indicate a particle having a large number of fine pores. The preferable ranges of the average particle diameter, specific surface area and pore diameter of the porous particles are described later.

One embodiment of the porous particles used in the present invention is porous particles of a (meth)acrylic polymer having a crosslinked structure and a hydroxyl group. Another embodiment is porous particles of at least one selected from a (meth)acrylic polymer, a vinyl acetate polymer, polysaccharides, silica and glass. These are described in detail below.

The porous particles are preferably porous particles of at least one selected from a (meth)acrylic polymer, a vinyl acetate polymer, polysaccharides, silica and glass, because unnecessary hydrophobic interaction between the porous particles and the steviol glycoside can be suppressed. Among these, for the reason that the unnecessary hydrophobic interaction between the porous particles and the steviol glycoside can be more suppressed, a (meth)acrylic polymer is preferred.

(1-1): (Meth)acrylic Polymer

The porous particles composed of a (meth)acrylic polymer includes, for example, porous particles having crosslinked structures, which are obtained by polymerizing a monomer containing a crosslinking (meth)acrylate. In the present description, the (meth)acrylic polymer means that 50% by mass or more, preferably 80% by mass or more, of monomers as raw materials constituting the polymer are composed of a (meth)acrylate. Accordingly, the porous particles of a (meth)acrylic polymer may be sufficient if 50% by mass or more of all constituent units of the polymer are a (meth)acrylate-derived constituent unit, and the porous particles may contain a constituent unit derived from a monomer other than (meth)acrylate. For the reason that the porous particles have an excellent hydrolysis resistance and an usable period of the obtained separation medium increases, the ratio of the constituent unit derived from (meth)acrylate to all constituent units of the polymer is preferably 50% by mass or more, more preferably 80% by mass or more, and still more preferably 90% by mass or more.

The production method for the porous particles composed of a (meth)acrylic polymer is described below.

The porous particles composed of a (meth)acrylic polymer, used in the present invention, are obtained as a spherical porous particle having a crosslinked structure typically by dispersing a monomer phase in which a monomer including 50% by mass or more of (meth)acrylate, a pore-forming agent, a polymerization initiator, etc. are contained, in an aqueous phase containing a dispersion stabilizer, etc., and performing a polymerization reaction by heating, etc.

The method for obtaining such porous particles can be performed by using a method disclosed, for example, in JP-B-S58-058026 and carrying out suspension polymerization or emulsion polymerization.

As the monomer of the raw material constituting the porous particles, a non-crosslinking monomer and a crosslinking monomer can be used. In order to configure porous particles having a crosslinked structure, a crosslinking monomer may be used as a monomer of a raw material.

The non-crosslinking monomer includes, for example, an alkyl (meth)acrylate such as methyl (meth)acrylate, ethyl (meth)acrylate, butyl (meth)acrylate, stearyl (meth)acrylate, 2-ethylhexyl (meth)acrylate and cyclohexyl (meth)acrylate; a (meth)acrylate having a reactive functional group; unsaturated carboxylic acids such as itaconic acid and maleic acid; aromatic vinyl monomers such as styrene, methylstyrene, ethylstyrene, α-methylstyrene, chlorostyrene and chloromethylstyrene; vinyl esters such as vinyl acetate and vinyl propionate; vinyl ethers such as methyl vinyl ether and ethyl vinyl ether; vinylpyridine; and vinylpyrrolidone. One of these non-crosslinking monomers may be used alone, or two or more thereof may be used in combination. Among these non-crosslinking monomers, a (meth)acrylate having a reactive functional group can immobilize polyethyleneimine and therefore, is preferred.

The (meth)acrylate having a reactive functional group encompasses a (meth)acrylate having a reactive functional group capable of immobilizing polyethyleneimine, and a (meth)acrylate having a functional group capable of reacting with a compound having such a reactive functional group (hereinafter, the compound is sometimes referred to as a "spacer"; details will be described later), and in the present invention, both can be used.

The reactive functional group of the (meth)acrylate having a reactive functional group includes, for example, a hydroxyl group, an amino group, a carboxyl group, a halogen group, and an epoxy group. Among these functional groups, an epoxy group is preferred, since the reactive functional group is easily introduced and the reactivity with polyethyleneimine is excellent. In addition, although details will be described later, when an epoxy group is used as the reactive functional group, the epoxy group remaining after immobilization reaction is preferably converted to a hydroxyl group by a post-treatment. More specifically, in the separation medium of the present invention, the porous (meth)acrylic polymer particle wherein polyethyleneimine is immobilized preferably has a hydroxyl group.

Specific examples of the (meth)acrylate having a reactive functional group include a (meth)acrylate containing a hydroxyl group such as hydroxyethyl (meth)acrylate, hydroxypropyl (meth)acrylate and glycerol mono(meth) acrylate; and a (meth)acrylate containing an epoxy group such as glycidyl (meth)acrylate, 4,5-epoxybutyl (meth)acrylate and 9,10-epoxy-stearyl (meth)acrylate. One of these (meth)acrylates having a reactive functional group may be used alone, or two or more thereof may be used in combination. Among these (meth)acrylates having a reactive functional group, for the reason that the reactive functional group is easily introduced and reactivity with polyethyleneimine is excellent, a (meth)acrylate containing an epoxy group is preferred, glycidyl (meth)acrylate is more preferred, and glycidyl methacrylate is still more preferred.

An used amount of the (meth)acrylate having a reactive functional group is preferably 5% by mass or more and 95% by mass or less, more preferably 10% by mass or more and 90% by mass or less, per 100% by mass of all monomers.

When the used amount of the (meth)acrylate having a reactive functional group is 5% by mass or more, the immobilization reaction of polyethyleneimine sufficiently proceeds, and the amount of the introduced polyethyleneimine is large enough, which leads to adsorption of a sufficient amount of steviol glycosides. On the other hand, when the used amount of the (meth)acrylate having a reactive functional group is 95% by mass or less, the pore structure sufficiently grows, and the obtained porous particle has an excellent mechanical strength.

The crosslinking monomer includes, for example, a crosslinking (meth)acrylate such as ethylene glycol di(meth)acrylate and polyethylene glycol di(meth)acrylate; and a crosslinking monomer other than (meth)acrylate, such as divinylbenzene, divinyl naphthalene, 2,4,6-trivinylethylbenzene, divinyl adipate, diallyl maleate, diallyl phthalate and triallyl 1,3,5-benzenetricarboxylate. One of these crosslinking monomers may be used alone, or two or more thereof may be used in combination. Among these crosslinking monomers, for the reason that the polymerization reactivity with the (meth)acrylate having a reactive functional group is excellent, a crosslinking (meth)acrylate is preferred, ethylene glycol di(meth)acrylate and polyethylene glycol di(meth)acrylate are more preferred, and ethylene glycol di(meth)acrylate is still more preferred.

An used amount of the crosslinking monomer is preferably 5% by mass or more and 95% by mass or less, more preferably 10% by mass or more and 90% by mass or less, per 100% by mass of all monomers.

When the used amount of the crosslinking monomer is 5% by mass or more, the pore structure sufficiently grows, and the obtained porous particle has an excellent mechanical strength. On the other hand, when the used amount of the crosslinking monomer is 95% by mass or less, the immobilization reaction of polyethyleneimine sufficiently proceeds, and the amount of the introduced polyethyleneimine is large enough, which leads to adsorption of a sufficient amount of steviol glycosides.

(1-2): Vinyl Acetate Polymer

The porous polymer composed of a vinyl acetate polymer includes, for example, a poly(vinyl acetate-triallyl isocyanurate) copolymer.

In the case of a poly(vinyl acetate-triallyl isocyanurate) copolymer, it is preferable to produce and obtain a hydroxyl group as the reactive functional group by hydrolyzing a vinyl acetate group.

(1-3): Polysaccharides

The porous particles composed of polysaccharides includes, for example, a crosslinked agarose particle, a crosslinked dextran particle, and a crosslinked cellulose particle, and all of these have a hydroxyl group as the reactive functional group and are therefore preferred.

(1-4): Silica and Glass

With respect to the porous silica and porous glass particles, the polyethyleneimine can be introduced, for example, by reacting an organosilicon compound having a reactive functional group, such as 3-glycidoxypropyltrimethoxysilane.

(2) Physical Properties of Porous Particle

1) Average Particle Diameter

The average particle diameter of porous particles constituting the separation medium of the present invention is preferably 1 μm or more and 1,000 μm or less.

As an example, porous particles having such an average particle diameter of a (meth)acrylic or vinyl acetate polymer can be produced by the suspension polymerization method described in JP-A-S64-54004.

The method for adjusting the average particle diameter of porous particles includes, for example, a method of controlling operating conditions of suspension polymerization such as selection of types and amounts of various monomers described above, selection of types and amounts of emulsifier and/or protective colloid, intensity of stirring (e.g., stirring rotation speed), or others.

In addition, the produced particles may be classified by mesh sieving, water separation, air separation or other methods to have a uniform particle diameter.

The more preferable average particle diameter may vary depending on the use or size of the packing column used but is 4 μm or more and 700 μm or less, and the still more preferable average particle diameter is 10 μm or more and 500 μm or less.

When the average particle diameter is not less than the lower limit, the pressure drop at packing the particles into the column and passing a liquid is reduced, so that the flow rate can be sufficiently increased, which leads to enhancement of productivity of the separation treatment. On the other hand, when the average particle diameter is not more than the upper limit, the column efficiency increases, and the adsorbed amount or separation performance is improved.

The average particle diameter can be measured by a known method. For example, the average particle diameter can be obtained by measuring 100 or more particles for the particle diameter by means of an optical microscope, and calculating the volume median diameter from the distribution thereof.

The uniformity coefficient as an indicator of the particle diameter distribution width is, usually, preferably smaller, since the pressure drop at packing the particles into the column and passing a liquid becomes small. If the uniformity coefficient becomes large, although a packing efficiency into the column becomes high, a pressure drop tends to increase.

2) Specific Surface Area, Pore Diameter

The specific surface area and pore diameter of the porous particles are measured by nitrogen adsorption method (BET method) and mercury intrusion method, respectively.

The specific surface area is preferably from 1 to 1,000 $m^2/g$, more preferably from 10 to 500 $m^2/g$.

The pore diameter is preferably 10 Å (1 nm) or more and 10,000 Å (1,000 nm) or less. The more preferable pore diameter is 20 Å or more and 5,000 Å or less, and the still more preferable value is 20 Å or more and 2,000 Å or less.

The mercury intrusion method is a method of pressuring mercury to intrude into open pores and calculating the diameter of the pore assumed to be cylindrical by the Washburn equation using the intruded mercury volume corresponding to the pressure value, and ISO 15901-1 is applied mutatis mutandis to this method.

The pore diameter is the modal diameter.

These pore diameter and specific surface area can be adjusted by controlling the type or amount of the polymerizable monomer used, the quantitative ratio between water and the monomer during polymerization, or with allowing a predetermined amount of an organic solvent inert to polymerization to be present together in the reaction system at the time of polymerization, controlling the type or amount of the solvent. Furthermore, these can also be adjusted by the type or amount of the polymerization initiator.

When the pore diameter is not less than the above-described lower limit value, polyethyleneimine to be immobilized easily enters pores, and the immobilization reaction sufficiently proceeds, facilitating entering also of steviol glycosides into pores of the particle. As a result, the amount of the adsorbed steviol glycosides is increased. On the other hand, when the pore diameter is not more than the above-described upper limit value, a space which does not contribute to adsorption is less likely to be formed inside of the pore, and this prevents the amount of the adsorbed steviol glycosides from decreasing and furthermore, allows for enhancement of the mechanical strength of the separation medium particles.

[1-2]. Polyethyleneimine

In the separation medium of the present invention, polyethyleneimine is immobilized to the porous particles described above. In this connection, the polyethyleneimine is preferably immobilized to the porous particles by covalent bonding.

The polyethyleneimine for use in the present invention preferably has a mass average molecular weight (hereinafter, sometimes simply referred to as "molecular weight") of 200 or more and 100,000 or less. The molecular weight of polyethyleneimine is more preferably 300 or more, still more preferably 500 or more, and is more preferably 100,000 or less, and still more preferably 10,000 or less. Since it is presumed that in the separation medium of the present invention, polyethyleneimine serving as the functional group interacts three-dimensionally with the target steviol glycoside to be separated and the separation property is thereby enhanced, when the molecular weight is 200 or more, the degree of interaction with the target steviol glycoside to be separated increases. When the molecular weight is 100,000 or less, the viscosity is kept from becoming too high, and dilution with a large amount of solvent is not necessary at the time of immobilization reaction, and the reaction rate of the immobilization reaction is enhanced to increase the amount introduced into the separation medium, as a result, the amount of the adsorbed steviol glycoside increases.

In this connection, the molecular weight as used herein is a representative value and specifically, indicates the molecular weight shown on industrial polyethyleneimine, sold from Nippon Shokubai Co., Ltd. (trade name: Epomine) or reagent polyethyleneimine, etc. sold from various reagent companies.

In addition, the molecular weight of polyethyleneimine can also be determined using a size exclusion chromatography method, etc. after isolating polyethyleneimine, for example, by a method in which polyethyleneimine is desorbed from porous particles constituting the separation medium by hydrolysis reaction, etc. or porous particles constituting the separation medium are solubilized in a solvent and after that, the porous particles-constituting compound and polyethyleneimine are separated.

(1) Reactive Functional Group of Porous Particles

As an example of a method for immobilizing the above-described polyethyleneimine to porous particles, although a method usually employed as a method for immobilizing a (meth)acrylic polymer having a crosslinked structure to porous particles is described below, the method is not limited thereto. The same method can be employed also in the case of using porous particles of a vinyl acetate polymer, polysaccharides, silica or glass in place of the porous (meth)acrylic polymer particles.

For the immobilization, a method in which a (meth) acrylate having a reactive functional group-imparting property is incorporated in the form of a copolymer, etc. into a (meth)acrylic polymer particle and thereafter, the reactive functional group and polyethyleneimine are directly reacted, or a method in which bonding is achieved via a low molecular or high molecular compound (spacer) containing in a molecule one or more functional groups capable of reacting with a functional group included in constituent components of a (meth)acrylic polymer and one or more functional groups capable of reacting with polyethyleneimine.

For example, as the former method, there is exemplified a method in which a functional group for forming a covalent bond with an amino group, such as epoxy group and carboxyl group, is incorporated into a (meth)acrylic polymer particle and polyethyleneimine is directly reacted with the functional group and thereby immobilized.

As the latter method, for example, there are a method in which using amino acids (aminocarboxylic acids) as the spacer, the amino group moiety is reacted with an epoxy group of a (meth)acrylic polymer and thereafter, a carboxyl group at another end is reacted with an amino group of polyethyleneimine, and a method in which using, as the spacer, a polyglycidyl compound such as (poly)ethylene glycol diglycidyl ether and polyol polyglycidyl ether, a hydroxyl group or an amino group in a (meth)acrylic polymer is bonded to one end of the polyglycidyl compound and polyethyleneimine is bonded to an epoxy group at the remaining end.

In this connection, as the spacer, it is preferable to use a spacer having a linear structure, and in this case, there is a tendency that reactivity with polyethyleneimine or steric hindrance to the porous (meth)acrylic polymer particles during immobilization is reduced and the adsorbed amount increases.

(2) Polyethyleneimine Immobilization Reaction

In the polyethyleneimine immobilization reaction, for example, polyethyleneimine as it is or in the form of an organic solvent solution or an aqueous solution is supplied to porous particles of the above-described (meth)acrylic polymer having an epoxy group, etc. and allowed to undergo a reaction.

For the reason that sole use of polyethyleneimine leads to high viscosity and poses a problem associated with equipment in the industrial production, the polyethyleneimine is preferably supplied in the form of an organic solvent solution or an aqueous solution to porous particles of the (meth)acrylic polymer having an epoxy group, etc., and furthermore, in the case of using porous particles of a (meth)acrylic polymer having an epoxy group, it is particularly preferable to supply the polyethyleneimine in the form of an organic solvent solution to the porous particles of the (meth)acrylic polymer having an epoxy group, etc., because in an aqueous solution system, the reaction becomes a competitive reaction to the diol formation reaction due to addition of water to an epoxy group.

The organic solvent is preferably a solvent capable of dissolving polyethyleneimine, and examples thereof include alcohols such as butyl alcohols, propyl alcohols, ethyl alcohol and methyl alcohol, ethers such as ethylene glycol dimethyl ether, diethylene glycol dimethyl ether, diethyl ether, tetrahydrofuran (THF), cyclopentyl methyl ether, 4-methyltetrahydropyran and dioxane, and amides such as dimethylformamide and dimethylacetamide. Among these, ethers capable of causing swelling of porous particles of the (meth)acrylic polymer having an epoxy group, etc., such as ethylene glycol dimethyl ether, diethylene glycol dimethyl ether, diethyl ether, THF and dioxane, are more preferred.

The immobilization reaction temperature is preferably on the order of 20 to 100° C. When the temperature is 20° C. or more, the reaction time can be shortened, whereas when the temperature is 100° C. or less, decomposition of the porous (meth)acrylic polymer particle can be suppressed.

(3) Post-Treatment

After the immobilization reaction is performed as described above, the reactive functional group remaining on the porous particles side is preferably inactivated by a post-treatment. The reactive functional group which remains without being deactivated may gradually react with an active group of foreign substances in the steviol glycoside or stevia leaf extract to decrease the adsorption capacity of the separation medium or deteriorate the separation selectivity.

For example, in the case where the reactive functional group is an epoxy group, examples of the post-treatment include a method of converting the epoxy group to a hydroxyl group (i.e., diol) by the reaction with water. The catalyst used here includes an aqueous solution of an inorganic acid such as phosphoric acid and sulfuric acid, and an aqueous solution of alkalis such as sodium hydroxide and potassium hydroxide, and in particular, use of an aqueous sulfuric acid solution is preferred. Although the treatment conditions such as aqueous sulfuric acid solution concentration, reaction temperature and reaction time are not particularly limited, the treatment can be conducted usually for 0.1 to 24 hours under the conditions of a concentration of 1 to 30% by mass and a temperature of 10 to 90° C. More preferable treatment conditions are a concentration of 3 to 20% by mass, a temperature of 20 to 80°C, and from 1 to 10 hours.

[1-3]. Characteristic Features of Separation Medium (1) Average Particle Diameter The average particle diameter of the separation medium of the present invention is preferably 1 µm or more and 1,000 µm or less. The average particle diameter of the separation medium reflects the average particle diameter of the porous particles used but is larger generally by approximately from 0 to 20% than the average particle diameter of the porous particles used due to immobilization of polyethyleneimine. The more preferable average particle diameter may vary depending on the use or size of the packing column used but is 4 µm or more and 700 µm or less, and the still more preferable average particle diameter is 10 µm or more and 500 µm or less.

When the average particle diameter is not less than the lower limit, the pressure drop at packing the particles into the column and passing a liquid is reduced, so that the flow rate can be sufficiently increased, leading to enhancement of productivity of the separation treatment. On the other hand, when the average particle diameter is not more than the upper limit, the column efficiency increases, and the adsorbed amount or separation performance is improved.

The average particle diameter can be measured by a known method. For example, 100 or more particles are measured for the particle diameter by means of an optical microscope, and the average particle diameter can be obtained by calculating the volume median diameter from the distribution thereof.

The uniformity coefficient as an indicator of the particle diameter distribution width is, usually, preferably smaller, because the pressure drop at packing the particles into the column and passing a liquid becomes small. If the uniformity coefficient becomes large, although the packing efficiency into the column may become high, the pressure drop tends to increase.

(2) Specific Surface Area, Pore Diameter

The specific surface area of the separation medium is measured by nitrogen adsorption method (BET method), and the pore diameter and pore volume are measured the mercury intrusion method. The specific surface area and pore volume of the separation medium reflect the specific surface area and pore volume of the porous particles used but are subject to a change of approximately 0 to 50% due to the polyethyleneimine-immobilized state.

The specific surface area is preferably from 1 to 1,000 $m^2/g$, and more preferably from 10 to 500 $m^2/g$.

The pore diameter is preferably 10 Å or more and 10,000 Å or less. The more preferable pore diameter is 20 Å or more and 5,000 Å or less, and the still more preferable value is 20 Å or more and 2,000 Å or less.

The pore diameter is the modal diameter.

When the pore diameter is not less than the lower limit value, at the time of production of the separation medium, a target compound to be separated easily enters pores, and the immobilization reaction sufficiently proceeds. In addition, in the separation and purification step for steviol glycosides by use of the separation medium produced, the steviol glycosides easily enter pores, as a result, the amount of the adsorbed steviol glycosides is increased. On the other hand, when the pore diameter is not more than the upper limit value, a space which does not contributes to adsorption is less likely to be formed inside of the pore, and this prevents the amount of the adsorbed steviol glycosides from decreasing and furthermore, allows for enhancement of the mechanical strength of the separation medium particles.

The pore volume is preferably 0.1 mL/g or more and 3.0 mL/g or less. The more preferable pore volume is 0.2 mL/g or more and 2.5 mL/g or less, and the still more preferable value is 0.5 mL/g or more and 2.0 mL/g or less.

(3) Nitrogen Content Rate, Total Ion-Exchange Capacity

The amount of the immobilized polyethyleneimine can be quantitatively determined by measuring the nitrogen content rate (N content) by elemental analysis or the total ion-exchange capacity of the separation medium obtained.

The nitrogen content rate is preferably 0.3% by mass or more. The upper limit thereof is not particularly limited but is usually 30% by mass or less.

When the nitrogen content rate is 0.3% by mass or more, the amount of the adsorbed steviol glycosides is increased, and the efficiency of the separation medium increases. On the other hand, when the nitrogen content rate is 30% by mass or less, the proportion of a portion occupied by polyethyleneimine in the space inside pores of the separation medium falls within a proper range, and steviol glycosides are allowed to appropriately diffuse and penetrate, which leads to an increase in the adsorbed amount.

For the same reason, the total ion-exchange capacity of the separation medium is 0.1 milliequivalents/g or more and 20 milliequivalents/g or less, preferably 0.1 milliequivalents/g or more and 10 milliequivalents/g or less.

With respect to the method for measuring the total ion-exchange capacity, a separation medium sample corresponding to 0.5 to 1.5 g of the dry separation medium is precisely weighed and shaken at 30° ° C. for 8 hours in 250 mL of an aqueous 0.2 N—HCl solution, and after obtaining the HCl concentration in the supernatant, the total ion-exchange capacity can be determined by calculation.

(4) Use

The separation medium of the present invention can separate two or more types of steviol glycosides as described later and is preferably used as the separation medium for steviol glycoside separation.

[2] Separation Method Using Separation Medium of the Present Invention

The separation medium of the present invention is suitably used for separating two or more types of steviol glycosides, preferably rebaudioside A, and more preferably stevioside and rebaudioside A, by using these as the separation target.

The method for separating respective steviol glycosides from a solution containing two or more types of steviol glycosides includes the following two separation methods.

(A) A steviol glycoside separation method including a liquid chromatography step of loading a solution containing two or more types of steviol glycosides to the separation medium of the present invention, and allowing a solvent A to flow through the separation medium, thereby separating at least two types of steviol glycosides in the steviol glycoside group.

(B) A steviol glycoside separation method for obtaining two or more fractions containing different steviol glycosides as a main component, including an adsorption step of brining a solution containing two or more types of steviol glycosides and a solvent B into contact with the separation medium of the present invention to adsorb a steviol glycoside group to the separation medium, and an elution step of eluting the steviol glycoside group from the separation medium by using a solvent C.

In this connection, for convenience of description, although the solvent used in the liquid chromatography step is designated as solvent A, the solvent used in the adsorption step is designated as solvent B, and the solvent used in the elution step is designated as solvent C, these may be the same solvent or may be different solvents.

In both methods, a specific steviol glycoside can be separated from a solution containing a plurality of steviol glycosides. The steviol glycoside includes stevioside, steviolbioside, rebaudiosides A, B, C, D, E, F, G, H, I, J, K, L, M, N and O, and dulcosides A and B. It is preferred that at least rebaudioside A can be separated in high purity from a steviol glycoside group consisting of two or more types selected from the steviol glycosides above, and it is more preferred that stevioside and rebaudioside A as main components of the stevia leaf can be separated with high efficiency.

Specifically, in the case where the solution containing two or more types of steviol glycosides contains rebaudioside A, a main component is preferably rebaudioside A out of a steviol glycoside group contained in at least one fraction obtained in the liquid chromatography step or elution step, i.e., preferably 90% by mass or more, and more preferably 93% by mass or more, is rebaudioside A.

In another preferred example, in the case where the solution containing two or more types of steviol glycosides contains stevioside and rebaudioside A, as the fractions obtained in the liquid chromatography step or elution step, 90% by mass or more of respective contents of stevioside and rebaudioside A contained in the solution are eluted in different fractions. This means that the ability to separate stevioside and rebaudioside A as main components of the stevia leaf is high, which is preferred because higher-purity rebaudioside A can be easily obtained with high efficiency The steviol glycoside group adsorbed to the separation medium in the adsorption step need not be all steviol glycosides contained in the solution above, and it may be sufficient if at least one or more objective steviol glycosides as the separation target are adsorbed.

The separation treatment for separating stevioside and rebaudioside A from a solution containing, as the steviol glycoside group, at least stevioside and rebaudioside A can be performed according to the following steps.

(A-1) A step of loading a solution containing a steviol glycoside group including stevioside and rebaudioside A extracted from stevia leaves, etc. to a column packed with the separation medium of the present invention, and allowing a solvent A to flow through the column to separate stevioside and rebaudioside A by chromatography.

(B-1) A step of bringing a solution containing a steviol glycoside group including stevioside and rebaudioside A extracted from stevia leaves, etc. and a solvent B into contact with the separation medium of the present invention to adsorb the steviol glycoside group to the separation medium, and (B-2) a step of subsequently eluting steviol glycosides from the separation medium to which the steviol glycoside group is adsorbed, by using a solvent C.

(BB-1) A step of bringing a solution containing a steviol glycoside group including stevioside and rebaudioside A extracted from stevia leaves, etc. and a solvent B into contact with the separation medium of the present invention to adsorb the steviol glycoside group to the separation medium, (BB-2) a step of subsequently eluting the steviol glycoside group mainly including stevioside from the separation medium to which the steviol glycoside group is adsorbed, by using a solvent C1, and (BB-3) a step of subsequently eluting the steviol glycoside group mainly including rebaudioside A from the separation medium to which the steviol glycoside group is adsorbed, by using a solvent C2.

In this connection, although the solvent used in (BB-2) and the solvent used in (BB-3) are referred to as solvent C1 and solvent C2, respectively, both of these are one embodiment of the solvent C used in the elution step, and the solvent C1 and the solvent C2 may be the same solvent or may be different solvents.

(BBB-1) A step of bringing a solution containing a steviol glycoside group including rebaudioside A extracted from stevia leaves, etc. and a solvent B into contact with the separation medium of the present invention to adsorb mainly the rebaudioside A glycoside group to the separation medium, and (BBB-2) a step of subsequently eluting steviol glycosides from the separation medium to which the steviol glycoside group containing rebaudioside A as a main component is adsorbed, by using a solvent C.

The objective steviol glycoside can be separated with good selectivity by these methods.

In these separation treatments, although a treatment method such as batch treatment method and column treatment method is used, a column treatment method using a column containing the separation medium above and having at least one container is preferred.

Each of the solvent A, solvent B and solvent C may be independently a solvent capable of dissolving steviol glycosides, and examples thereof include butyl alcohols such as isobutyl alcohol [solubility parameter: 21.5 $MPa^{(1/2)}$], n-butyl alcohol [solubility parameter: 23.3 $MPa^{(1/2)}$], secbutyl alcohol [solubility parameter: 22.1 MPa$^{(1/2)}$] and tert-butyl alcohol [solubility parameter: 21.7 MPa$^{(1/2)}$], propyl alcohols such as 1-propyl alcohol [solubility parameter: 24.3 MPa$^{(1/2)}$] and 2-propyl alcohol [solubility parameter: 23.5 MPa$^{(1/2)}$], alcohols such as ethyl alcohol [solubility parameter: 26.0 MPa$^{(1/2)}$], methyl alcohol [solubility parameter: 29.7 MPa$^{(1/2)}$], etc., (poly)ethylene glycols such as ethylene glycol [solubility parameter: 29.9 MPa$^{(1/2)}$], diethylene glycol [solubility parameter: 24.8 MPa$^{(1/2)}$], etc., polyols such as glycerol [solubility parameter: 33.8 MPa$^{(1/2)}$] etc., ethers such as ethylene glycol dimethyl ether [solubility parameter: 17.6 MPa$^{(1/2)}$], diethylene glycol dimethyl ether, diethyl ether [solubility parameter: 15.1 MPa$^{(1/2)}$], THF [solubility parameter: 18.6 MPa$^{(1/2)}$], dioxane [solubility parameter: 20.5 MPa$^{(1/2)}$], etc., amides such as dimethylformamide [solubility parameter: 24.8 MPa$^{(1/2)}$], dimethylacetamide [solubility parameter: 22.1 MPa$^{(1/2)}$], etc., and water [solubility parameter: 47.9 MPa$^{(1/2)}$], and the solvent A and the solvent B are preferably a solvent having high solubility for steviol glycosides.

With respect to all of the solvent A, solvent B and solvent C, alcohols such as tert-butyl alcohol, propyl alcohols, ethyl alcohol and methyl alcohol, (poly)ethylene glycols, and glycerol, which are freely miscible with water, are more preferred, and the solvent B is particularly preferably a solvent containing propyl alcohol, ethyl alcohol or methyl alcohol having high adsorption capacity for steviol glycosides. On the other hand, the solvent A is preferably a mixed solvent in which a concentration is reduced by mixing water or methanol with propyl alcohols and ethyl alcohol.

The action mechanism for separating steviol glycosides is presumed to be based on hydrophilic interaction chromatography and therefore, as the solvent C, it is preferable to use a solvent having high polarity in comparison with the solvent B or use a mixed solvent obtained by mixing a high-polarity solvent and water with the solvent B. In addition, when elution is performed using two or more types of solvents separately as the solvent C, two or more fractions containing different steviol glycosides as respective main components can be obtained. With respect to the two or more types of solvents used as the solvent C, for example, a method of combining two or more different types selected from the solvents recited above, or a method of selecting two types of solvents and changing the mixing ratio in two or more ways, may be selected. However, it is only necessary to select two or more types of solvents capable of adjusting the hydrophilic interaction between the separation medium and the target steviol glycoside to be separated.

In this connection, the solubility parameter encompassing the degree of contribution of the polarity, which serves as the indicator for judging the polarity of the solvent, is preferably 15 MPa$^{(1/2)}$ or more, and particularly preferably 18 MPa$^{(1/2)}$ or more. Here, the solubility parameter shown for each solvent refers to the value described in Polymer Handbook, 3rd ed. (issued 1989), WILEY.

When the separation medium of the present invention is used, decolorization of the color component in the solution containing the steviol glycoside group can also be performed at the same time in the liquid chromatography step or elusion step, which is preferable. In the case of using the separation medium of the present invention, since the color component remains in the column in both of the liquid chromatography step and the elution step, such a color component can be removed from a fraction containing, as a main component, a steviol glycoside to be separated. The color component remaining in the column can be separately eluted and used by regenerating the separation medium.

According to the above-described separation method, steviol glycosides can be produced using a step of separating at least two types of steviol glycosides from a solution containing two or more types of steviol glycosides, and a step that is conventionally known as a production method for steviol glycosides.

EXAMPLES

Although the present invention is described more specifically below by referring to Examples, the present invention is not limited to the descriptions in the following Examples as long as its gist is observed.

[Evaluation Methods of Physical Properties]

The methods for evaluating the physical properties of the separation media obtained in the following Examples and Comparative Examples are as follows.

<Average Particle Diameter>

The average particle diameter was obtained by measuring 100 or more particles for the particle diameter and calculating the volume median diameter from the distribution thereof.

<Specific Surface Area>

The specific surface area was measured by the nitrogen gas adsorption method. The nitrogen gas adsorption method is a method of determining the monolayer adsorbed amount by using the BET equation from the change in pressure before and after adsorption, and the specific surface area can be calculated from a cross-sectional area of one molecule of nitrogen gas.

The sample resin particles subjected to a drying treatment were weighed, and the specific surface area was measured by means of Flowsorb Model III manufactured by Micromeritics Instrument Corp.

<Pore Volume, Pore Diameter>

The pore volume and pore diameter were measured by the mercury intrusion method using AutoPore 9520 manufactured by Micromeritics Instrument Corp.

<Total Ion-Exchange Capacity>

With respect to the method for measuring the total ion-exchange capacity, a separation medium sample corresponding to 0.5 to 1.5 g of the dry separation medium was precisely weighed and shaken at 30° ° C. for 8 hours in 250 mL of an aqueous 0.2 N—HCl solution, and after obtaining the HCl concentration in the supernatant, the total ion-exchange capacity was determined by calculation.

<Nitrogen Content Rate>

The nitrogen content rate was measured by elemental analysis using CHN Analyzer 2400II manufactured by Perkin Elmer Inc.

[Production of Separation Medium]

Example 1

To 40 parts by mass of a mixture of a plurality of lots of porous (meth)acrylic polymer particles containing 70 parts by mass of glycidyl methacrylate and 30 parts by mass of ethylene glycol dimethacrylate and having an average particle diameter of 30 μm, a specific surface area of 49 to 56 m$^2$/g, a pore diameter of 382 to 522 Å, and a pore volume of 0.88 to 0.98 mL/g, 140 Parts by mass of diethylene glycol dimethyl ether and 60 parts by mass of polyethyleneimine (produced by Junsei Chemical Co., Ltd., reagent, molecular weight: 600) were added and the mixture was stirred to form a suspension state. The resulting suspension was heated to 80° C. and reacted for 6 hours. After cooling, porous particles wherein polyethyleneimine was immobilized were washed with water.

To the porous particles after water washing wherein polyethyleneimine was immobilized, 200 parts by mass of an aqueous 10% by mass sulfuric acid solution was added, and the mixture was stirred to form a suspension state. The resulting suspension was heated to 50° C. and held for 5 hours to conduct a diol formation reaction by the addition of water to an unreacted epoxy group.

After cooling, the porous particles were washed with water, and regeneration of the ion exchange group was performed using an aqueous 2 N sodium hydroxide solution to obtain Separation Medium 1.

In Separation Medium 1, the average particle diameter was 35 μm, the total ion-exchange capacity was 3.25 milliequivalents/g, the nitrogen content rate by elemental analysis was 5.7% by mass, the specific surface area was 38 m$^2$/g, the pore diameter was 782 Å, and the pore volume was 0.88 mL/g.

Example 2

To 40 parts by mass of porous (meth)acrylic polymer particles containing 70 parts by mass of glycidyl methacrylate and 30 parts by mass of ethylene glycol dimethacrylate and having a specific surface area of 36 m$^2$/g, a pore diameter of 1,204 Å, and a pore volume of 0.93 mL/g, 140 Parts by mass of diethylene glycol dimethyl ether and 60 parts by mass of polyethyleneimine (produced by Junsei Chemical Co., Ltd., reagent, molecular weight: 1,200) were added and the mixture was stirred to form a suspension state. The resulting suspension was heated to 80° C. and reacted for 6 hours. After cooling, porous particles wherein polyethyleneimine was immobilized were washed with water.

The porous particles after water washing wherein polyethyleneimine was immobilized were subjected to a diol formation reaction and regeneration of the ion exchange group in the same manner as in Example 1, and particles having a particle diameter of 75 to 220 μm were selected using a sieve mesh to obtain Separation Medium 2.

In Separation Medium 2, the total ion-exchange capacity was 2.20 milliequivalents/g, the nitrogen content rate by elemental analysis was 3.8% by mass, the specific surface area was 32 m$^2$/g, the pore diameter was 1,204 Å, and the pore volume was 0.80 mL/g.

Example 3

To 40 parts by mass of porous (meth)acrylic polymer particles containing 70 parts by mass of glycidyl methacrylate and 30 parts by mass of ethylene glycol dimethacrylate and having a specific surface area of 38 m$^2$/g, a pore diameter of 1,204 Å, and a pore volume of 1.07 mL/g, 140 Parts by mass of diethylene glycol dimethyl ether and 60 parts by mass of polyethyleneimine (produced by Junsei Chemical Co., Ltd., reagent, molecular weight: 1,200) were added and the mixture was stirred to form a suspension state. The resulting suspension was heated to 80° C. and reacted for 6 hours. After cooling, porous particles wherein polyethyleneimine was immobilized were washed with water.

The porous particles after water washing wherein polyethyleneimine was immobilized were subjected to a diol formation reaction and regeneration of the ion exchange group in the same manner as in Example 1, and particles having a particle diameter of 150 to 500 μm were selected using a sieve mesh to obtain Separation Medium 3.

In Separation Medium 3, the total ion-exchange capacity was 1.98 milliequivalents/g, the nitrogen content rate by elemental analysis was 3.4% by mass, the specific surface area was 28 m$^2$/g, the pore diameter was 1,504 Å, and the pore volume was 1.00 mL/g.

Example 4

To 40 parts by mass of porous (meth)acrylic polymer particles containing 60 parts by mass of glycidyl methacrylate and 40 parts by mass of ethylene glycol dimethacrylate and having a specific surface area of 127 m$^2$/g, a pore diameter of 1,204 Å, and a pore volume of 1.20 mL/g, 140 Parts by mass of diethylene glycol dimethyl ether and 60 parts by mass of polyethyleneimine (produced by Junsei Chemical Co., Ltd., reagent, molecular weight: 300) were added and the mixture was stirred to form a suspension state. The resulting suspension was heated to 80° C. and reacted for 6 hours. After cooling, porous particles wherein polyethyleneimine was immobilized were washed with water.

The porous particles after water washing wherein polyethyleneimine was immobilized were subjected to a diol formation reaction and regeneration of the ion exchange group in the same manner as in Example 1 to obtain Separation Medium 4.

In Separation Medium 4, the average particle diameter was 75 μm, the total ion-exchange capacity was 3.70 milliequivalents/g, the specific surface area was 95 m$^2$/g, the pore diameter was 302 Å, and the pore volume was 1.65 mL/g.

Example 5

To 40 parts by mass of porous (meth)acrylic polymer particles containing 70 parts by mass of glycidyl methacrylate and 30 parts by mass of ethylene glycol dimethacrylate and having a specific surface area of 37 m$^2$/g, a pore diameter of 942 Å, and a pore volume of 0.99 mL/g, 140 Parts by mass of diethylene glycol dimethyl ether and 60 parts by mass of polyethyleneimine (produced by Junsei Chemical Co., Ltd., reagent, molecular weight: 1,200) were added and the mixture was stirred to form a suspension state. The resulting suspension was heated to 80° C. and reacted for 6 hours. After cooling, reacted porous particles wherein polyethyleneimine was immobilized were washed with water.

The porous particles after water washing wherein polyethyleneimine was immobilized were subjected to a diol formation reaction and regeneration of the ion exchange group in the same manner as in Example 1 to obtain Separation Medium 5.

In Separation Medium 5, the average particle diameter was 139 μm, the total ion-exchange capacity was 2.21 milliequivalents/g, the specific surface area was 30 m$^2$/g, the pore diameter was 944 Å, and the pore volume was 0.80 mL/g.

Example 6

To 400 parts by mass of porous (meth)acrylic polymer particles containing 70 parts by mass of glycidyl methacrylate and 30 parts by mass of ethylene glycol dimethacrylate and having a specific surface area of 37 m$^2$/g, a pore diameter of 942 Å, and a pore volume of 0.99 mL/g, 1,400 Parts by mass of diethylene glycol dimethyl ether and 600 parts by mass of polyethyleneimine (produced by Wako Pure Chemical Industries, Ltd., reagent, molecular weight: 600)

were added and the mixture was stirred to form a suspension state. The resulting suspension was heated to 80° C. and reacted for 6 hours. After cooling, porous particles wherein polyethyleneimine was immobilized were washed with water.

The porous particles after water washing wherein polyethyleneimine was immobilized were subjected to a diol formation reaction and regeneration of the ion exchange group in the same manner as in Example 1 except that the amount of the aqueous 10% by mass sulfuric acid solution was changed to 2,000 parts by mass, and Separation Medium 6 was thereby obtained.

In Separation Medium 6, the average particle diameter was 140 μm, the total ion-exchange capacity was 2.99 milliequivalents/g, the specific surface area was 31 m$^2$/g, the pore diameter was 944 Å, and the pore volume was 0.85 mL/g.

Comparative Example 1

To 40 parts by mass of porous (meth)acrylic polymer particles containing 70 parts by mass of glycidyl methacrylate and 30 parts by mass of ethylene glycol dimethacrylate and having a specific surface area of 36 m$^2$/g, a pore diameter of 1,204 Å, and a pore volume of 0.93 mL/g, 160 Parts by mass of water and 40 parts by mass of tetraethylenepentamine (produced by Wako Pure Chemical Industries, Ltd., chemical grade) were added and the mixture was stirred to form a suspension state. The resulting suspension was heated to 80° C. and reacted for 6 hours. After cooling, porous particles wherein tetraethylenepentamine was immobilized were washed with water.

The porous particles after water washing wherein tetraethylenepentamine was immobilized were subjected to a diol formation reaction and regeneration of the ion exchange group in the same manner as in Example 1, and particles having a particle diameter of 75 to 220 μm were selected using a sieve mesh to obtain Separation Medium 7.

In Separation Medium 7, the nitrogen content rate by elemental analysis was 2.7% by mass.

Comparative Example 2

To 20 parts by mass of chloromethylated styrene-based porous particles containing 90 parts by mass of styrene and 10 parts by mass of divinylbenzene and having a specific surface area of 17 m$^2$/g, a pore diameter of 782 Å, and a pore volume of 0.39 mL/g, 38 Parts by mass of water, 32 parts by mass of sodium hydroxide and 40 parts by mass of toluene were added and the mixture was stirred to form a suspension state. The resulting suspension was, after adding 60 parts by mass of polyethyleneimine (produced by Wako Pure Chemical Industries, Ltd., reagent, molecular weight: 300), heated at 80° C. and reacted for 4 hours.

Following the reaction, toluene was removed by water vapor distillation and after cooling, porous particles wherein polyethyleneimine was immobilized were washed with water. Furthermore, regeneration of the ion exchange group was performed using an aqueous 2 N sodium hydroxide solution, and particles having a particle diameter of 300 to 1,180 μm were selected using a sieve mesh to obtain Separation Medium 8.

In Separation Medium 8, the total ion-exchange capacity was 6.66 milliequivalents/g, the specific surface area was 15 m$^2$/g, the pore diameter was 782 Å, and the pore volume was 0.34 mL/g.

[Evaluation Method of Separation Property]
(Separation Property Evaluation 1 by Chromatography)

Separation Medium 1 obtained in Example 1 was packed into a glass-made column having an inner diameter of 16 mm and a length of 100 mm. The column was connected to a high-performance liquid chromatograph, and high-performance liquid chromatography analysis was performed at a flow velocity of 1.00 mL/min by using an aqueous 90% ethanol solution as the solvent.

As a sample, 2 mg/mL aqueous 90% ethanol solution of each of stevioside and rebaudioside A (produced by Tokyo Chemical Industry Co., Ltd., reagent) was prepared, and 200 μL of each aqueous solution was loaded to the separation medium inside the column by injecting it into the column through which the solvent was allowed to flow. The chromatogram was measured with UV detector at a wavelength of 210 nm.

FIG. 1 illustrates the chromatogram. Elution peaks of stevioside and rebaudioside A stay away from each other in terms of retention time and stevioside and rebaudioside A can be completely separated.

(Separation Property Evaluation 2 by Chromatography)

Separation Medium 2 obtained in Example 2 or Separation Medium 7 obtained in Comparative Example 1 was packed into a polycarbonate-made column having an inner diameter of 9 mm and a length of 100 mm. The column was connected to a high-performance liquid chromatograph, and high-performance liquid chromatography analysis was performed at a flow velocity of 0.32 mL/min by using an aqueous 90% ethanol solution as the solvent.

As a sample, 2 mg/mL aqueous 90% ethanol solution of each of stevioside and rebaudioside A (produced by Tokyo Chemical Industry Co., Ltd., reagent) was prepared, and 63 μL of each aqueous solution was loaded to the separation medium inside the column by injecting it into the column through which the solvent was allowed to flow. The chromatogram was measured with UV detector at a wavelength of 210 nm.

Figure 2:
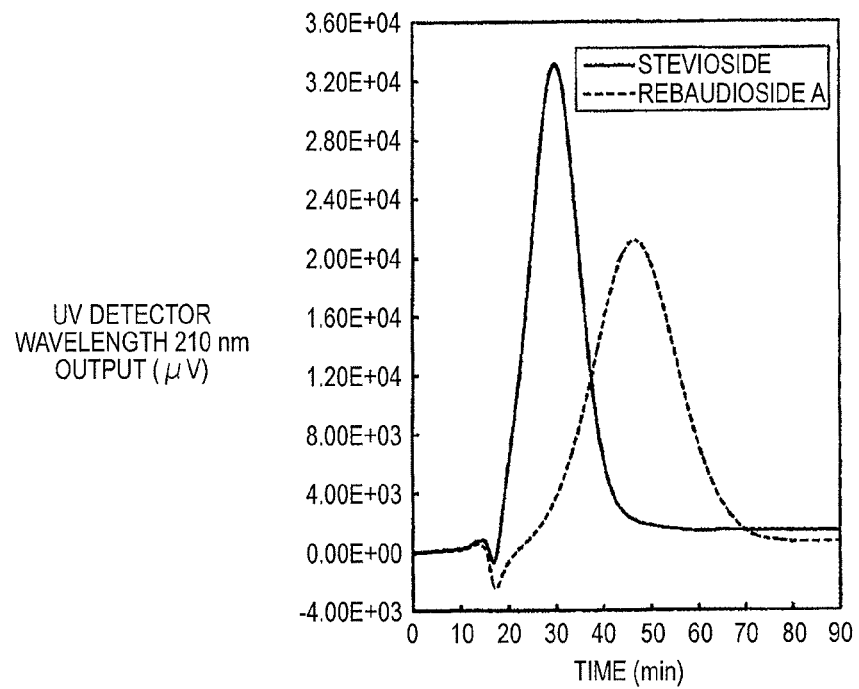
FIG. 2 is a graph illustrating results of performing evaluation of a separation property by chromatography using a separation medium of Example 2.
Figure 3:
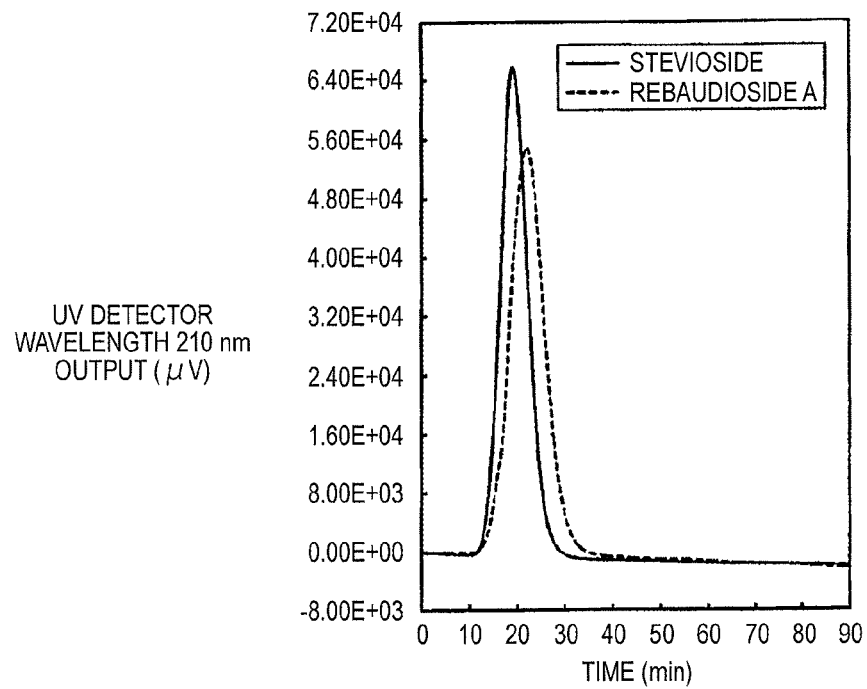
FIG. 3 is a graph illustrating results of performing evaluation of a separation property by chromatography using a separation medium of Comparative Example 1.

FIG. 2 illustrates the chromatogram for the column packed with Separation Medium 2 obtained in Example 2, and FIG. 3 illustrates the chromatogram for the column packed with Separation Medium 7 obtained in Comparative Example 1. With Separation Medium 2 of Example 2, stevioside and rebaudioside A are more spaced apart in terms of retention time, compared with Separation Medium 7 of Comparative Example 1, and the separation property is good.

(Separation Property Evaluation 3 by Chromatography)

Separation Medium 8 obtained in Comparative Example 2 was packed into a polycarbonate-made column having an inner diameter of 9 mm and a length of 100 mm. The column was connected to a high-performance liquid chromatograph, and high-performance liquid chromatography analysis was performed at a flow velocity of 0.32 mL/min by using an aqueous 70% ethanol solution as the solvent.

A 2 mg/mL aqueous 90% ethanol solution of each of stevioside and rebaudioside A (produced by Tokyo Chemical Industry Co., Ltd., reagent) was prepared as the sample, and 63 μL of each aqueous solution was loaded to the separation medium inside the column by injecting it into the column through which the solvent was allowed to flow. The chromatogram was measured with UV detector at a wavelength of 210 nm.

Figure 4:
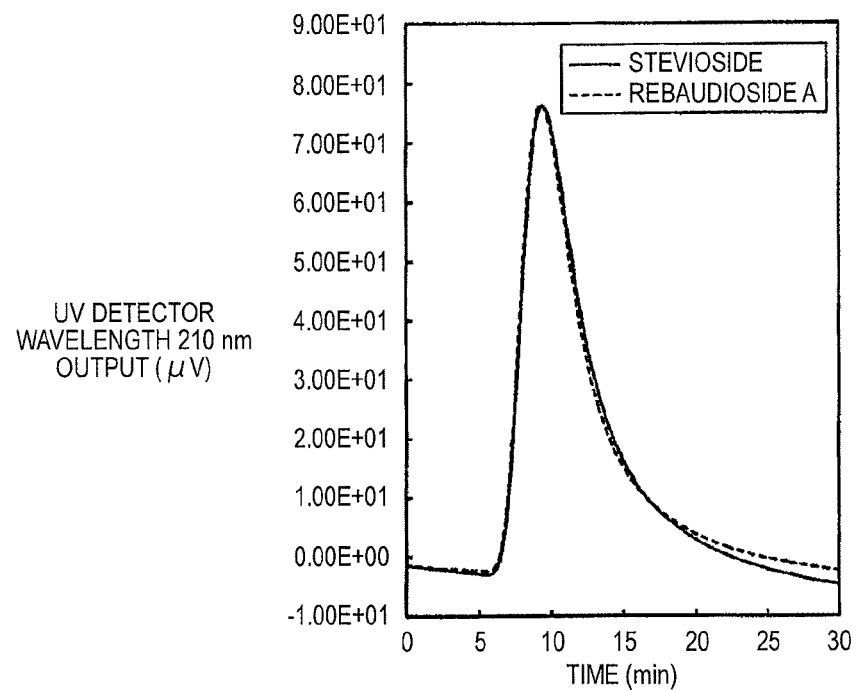
FIG. 4 is a graph illustrating results of performing evaluation of a separation property by chromatography using a separation medium of Comparative Example 2.

FIG. 4 illustrates the chromatogram for the column packed with Separation Medium 8 of Comparative Example 2. With Separation Medium 8 of Comparative Example 2, retention time of stevioside and rebaudioside A are completely identical, and thus, in the case of a separation medium in which polyethyleneimine is introduced into a polystyrene porous particles, despite a high total ion-exchange capacity, separation of stevioside and rebaudioside A was difficult due to unnecessary hydrophobic interaction between the porous particles and the steviol glycoside.
(Separation Property Evaluation 1 by Adsorption and Elution)

The solution containing steviol glycoside used in the separation property evaluation 1 by adsorption and elution was prepared according to the method described in "DIAION Manual 2 (issued by Mitsubishi Chemical Corporation), p. 304" and used in the form of an isopropyl alcohol solution.

More specifically, stevia leaves were extracted at 60° C. and after adding calcium chloride and magnesium oxide, filtration was performed to obtain an extract. The extract was passed through a synthetic adsorbent, DIAION SP700 (produced by Mitsubishi Chemical Corporation), to allow adsorption of steviol glycosides and then extruded by flushing. Subsequently, fractions eluted with an aqueous 85% methyl alcohol solution and furthermore, fractions extruded by flushing were combined to obtain an aqueous about 40% methyl alcohol solution of steviol glycosides. This solution was passed through a cation exchange resin, DIAION SK1BH (produced by Mitsubishi Chemical Corporation), to demineralize cation components and then passed through an anion exchange resin, DIAION HPA25L (produced by Mitsubishi Chemical Corporation), to perform demineralization of anion components and decolorization of color components. The obtained solution was further passed through a synthetic adsorbent, DIAION HP20 (produced by Mitsubishi Chemical Corporation), to allow adsorption of steviol glycosides, and a solution obtained after subsequent elution with 100% isopropyl alcohol was used.

Separation Medium 1 obtained in Example 1 was packed into a polycarbonate-made column having an inner diameter of 9 mm and a length of 100 mm. The column was connected to a high-performance liquid chromatograph, and an isopropyl alcohol solution of steviol glycosides (stevioside concentration: 1.43 g/L, rebaudioside A concentration: 0.44 g/L, stevioside/rebaudioside A=79/21, the value, as indicator of coloring components in the solution, obtained by dividing the value measured with UV-VIS spectrometer at a wavelength of 420 nm and an optical path length of 1 cm by the total concentration of stevioside and rebaudioside A: 0.003 AU/(mg/mL)) was passed through the column at a flow velocity of 0.63 mL/min for 60 minutes (stevioside supply amount: 54.4 mg, rebaudioside A supply amount: 16.8 mg).

Subsequently, ethyl alcohol was passed at a flow velocity of 0.63 mL/min for 10 minutes, an aqueous 95% ethyl alcohol solution was then passed at a flow velocity of 0.63 mL/min for 30 minutes, and an aqueous 90% ethyl alcohol solution was passed at a flow velocity of 0.63 mL/min for 40 minutes.

In the process above, fractions were collected every 2.5 minutes, and the contents of stevioside and rebaudioside A were determined by high-performance liquid chromatograph analysis with UV detector at a wavelength of 210 nm.

Figure 5:
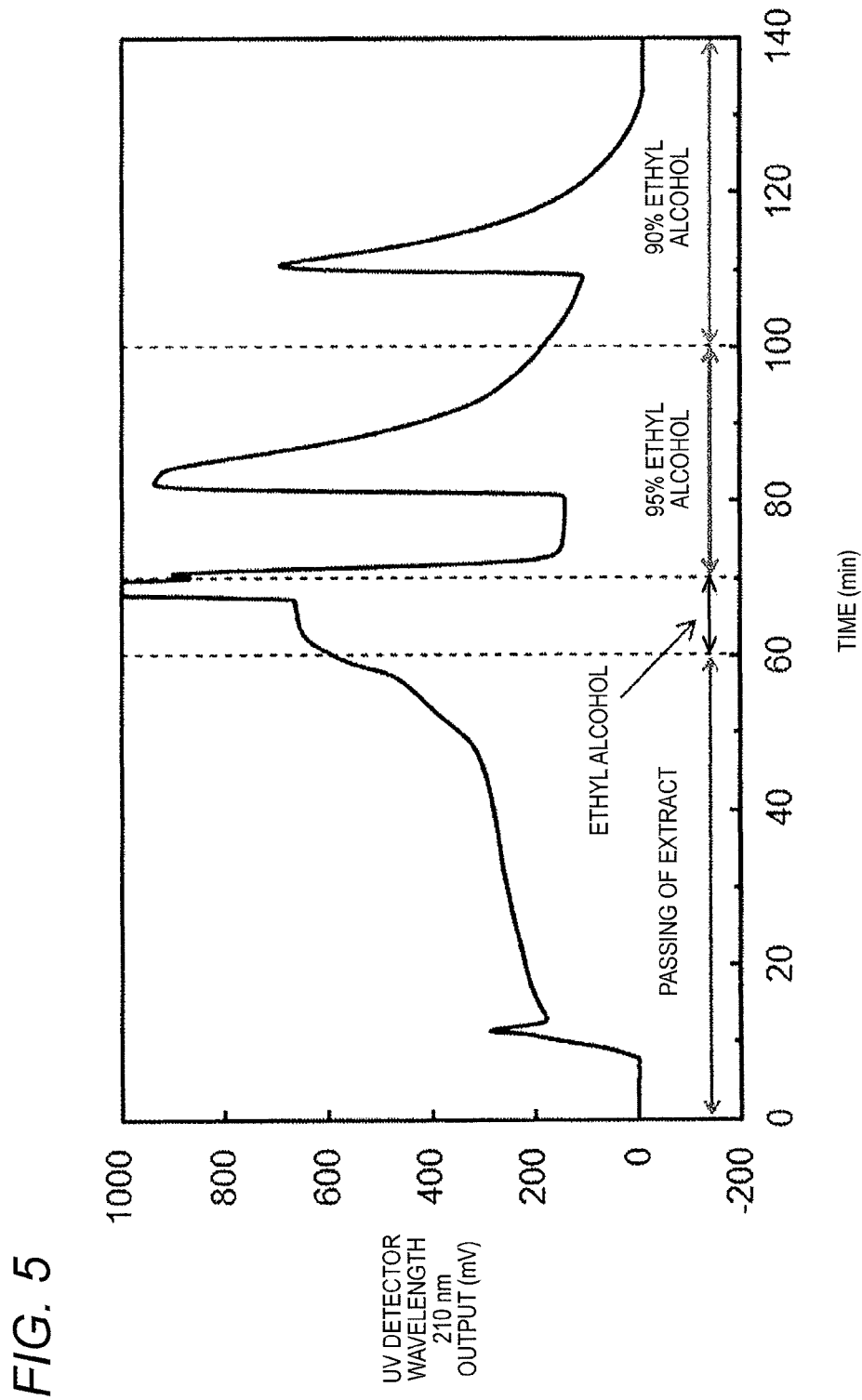
FIG. 5 is an adsorption and elution profile illustrating results of performing evaluation of a separation property by adsorption and elution using the separation medium of Example 1.
Figure 6:
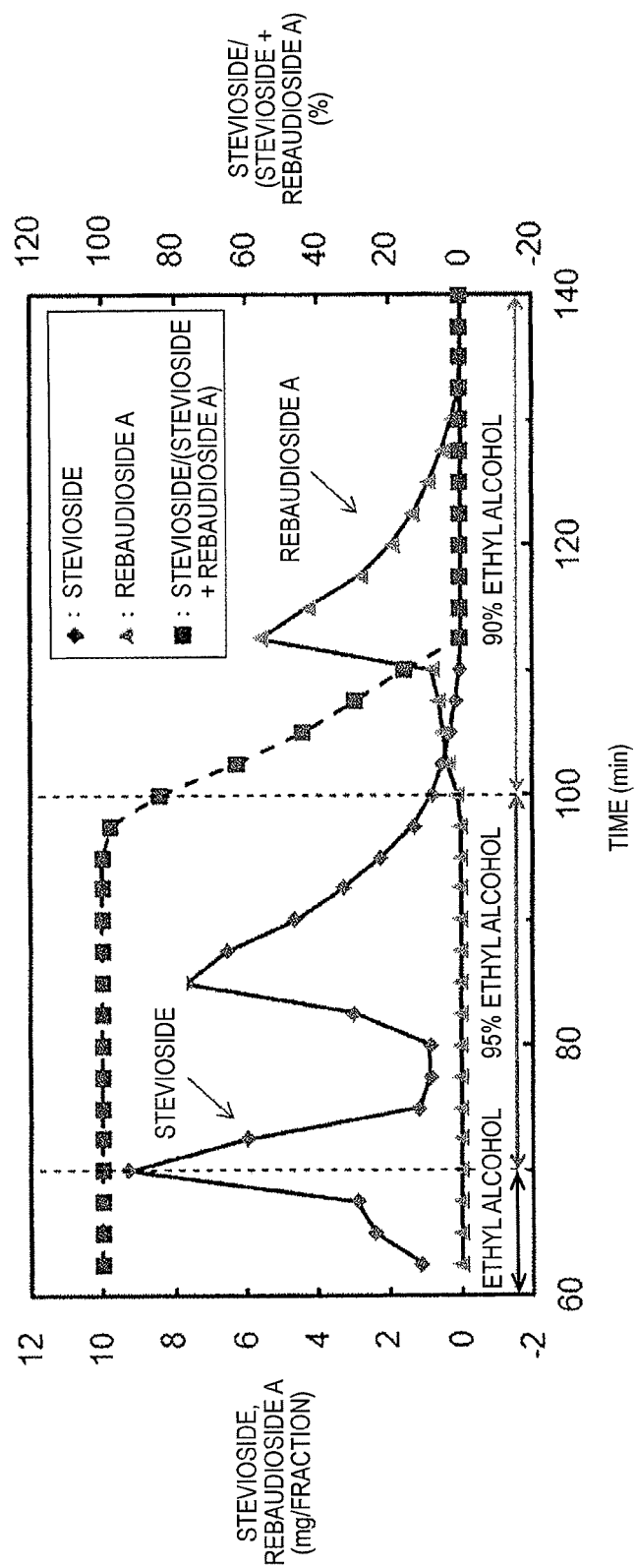
FIG. 6 is a graph illustrating contents of respective components and a ratio thereof as the results of performing evaluation of a separation property by adsorption and elution using the separation medium of Example 1.

FIG. 5 shows the adsorption and elution profile, and FIG. 6 shows the contents of stevioside and rebaudioside A in each fraction and (stevioside content)/(stevioside content+rebaudioside A content) (%).

In the fraction resulting from combining fractions at the time of passing of ethyl alcohol and a part of fractions at the time of passing of an aqueous 95% ethyl alcohol solution, the stevioside content was 42.6 mg, the rebaudioside A content was 0.0 mg, and (stevioside content)/(stevioside content+rebaudioside A content)=100%.

Furthermore, in the fraction resulting from combining a part of fractions at the time of passing of an aqueous 90% ethyl alcohol solution, the stevioside content was 0.0 mg, the rebaudioside A content was 17.6 mg, and (stevioside content)/(stevioside content+rebaudioside A content)=0%. In this connection, the content of rebaudioside A is larger than the supply amount, and this is presumed to be attributable to errors in the quantitative concentration at the high-performance liquid chromatograph analysis of fractions.
(Separation Property Evaluation 2 by Adsorption and Elution)

The solution containing steviol glycoside used in the separation property evaluation 2 by adsorption and elution was prepared according to the method described in "DIAION Manual 2 (issued by Mitsubishi Chemical Corporation), p. 304" except for omitting the step of adding calcium chloride and magnesium oxide and the step of decolorization by passing through an anion exchange resin, and used in the form of an isopropyl alcohol solution.

More specifically, stevia leaves were extracted at 60° C., and filtration was performed to obtain an extract. The extract was passed through a synthetic adsorbent, DIAION HP20 (produced by Mitsubishi Chemical Corporation), to allow adsorption of steviol glycosides and then extruded by flushing. Subsequently, fractions eluted with ethyl alcohol and furthermore, fractions extruded by flushing were combined to obtain an aqueous about 50% ethyl alcohol solution of steviol glycosides. This solution was passed through a cation exchange resin, DIAION SKIBH (produced by Mitsubishi Chemical Corporation), to demineralize cation components and then passed through a synthetic adsorbent, DIAION HP20 (produced by Mitsubishi Chemical Corporation), to allow adsorption of steviol glycosides, and a solution obtained after subsequent elution with 100% isopropyl alcohol was used.

Separation Medium 4 obtained in Example 4 was packed into a polycarbonate-made column having an inner diameter of 9 mm and a length of 100 mm. The column was connected to a high-performance liquid chromatograph, and an isopropyl alcohol solution of steviol glycosides (stevioside concentration: 3.64 g/L, rebaudioside A concentration: 2.27 g/L, stevioside/rebaudioside A=66/34, the value, as indicator of coloring components in the solution, obtained by dividing the value measured with UV-VIS spectrometer at a wavelength of 420 nm and an optical path length of 1 cm by the total concentration of stevioside and rebaudioside A: 0.169 AU/(mg/mL)) was passed through the column at a flow velocity of 0.44 mL/min for 42 minutes (stevioside supply amount: 67.4 mg, rebaudioside A supply amount: 42.1 mg).

Subsequently, isopropyl alcohol was passed at a flow velocity of 0.63 mL/min for 10 minutes, an aqueous ethyl alcohol solution was then passed at a flow velocity of 0.63 mL/min for 40 minutes, and an aqueous 95% ethyl alcohol solution was passed at a flow velocity of 0.63 mL/min for 40 minutes.

In the process above, fractions were collected every 2.5 minutes, and the contents of stevioside and rebaudioside A were determined by high-performance liquid chromatograph analysis.

Figure 7:
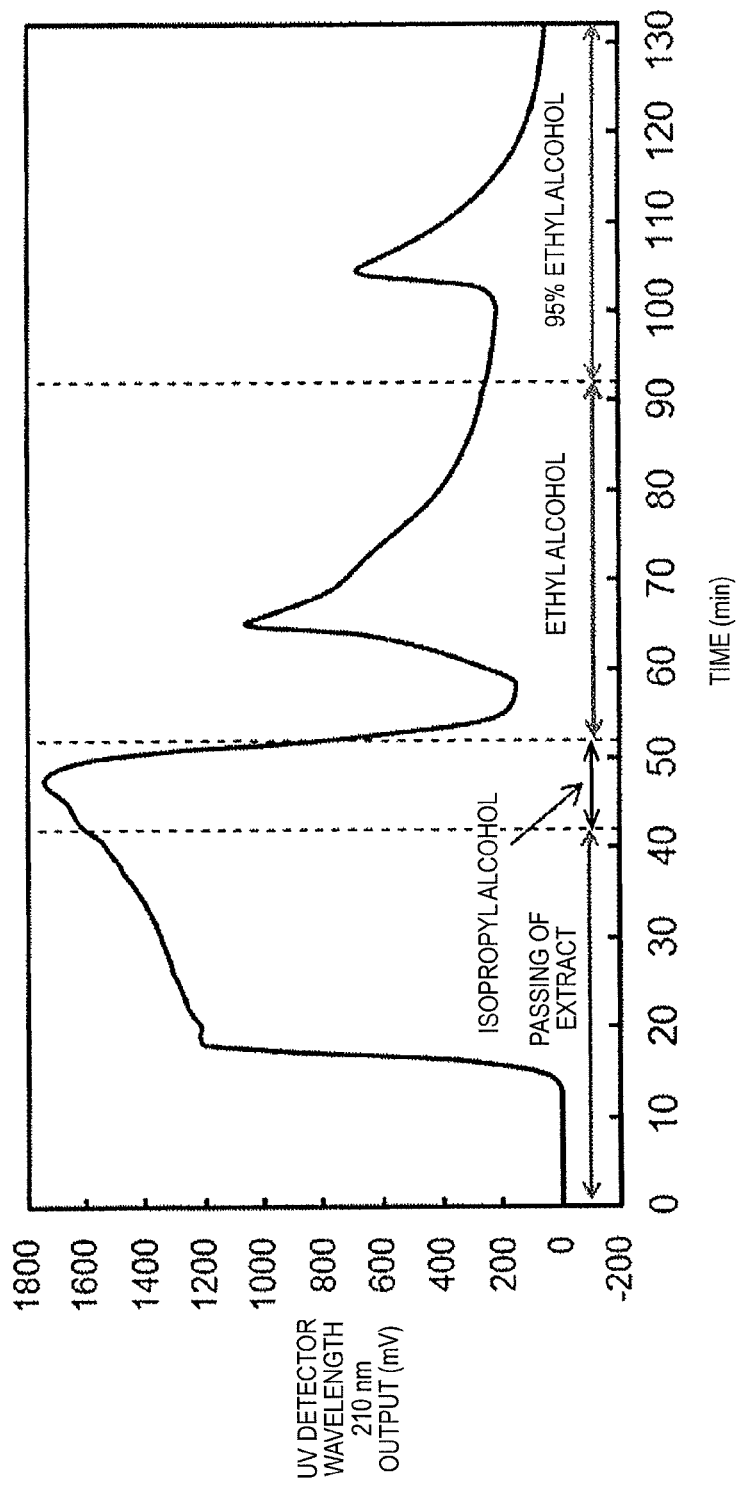
FIG. 7 is an adsorption and elution profile illustrating results of performing evaluation of the separation property by adsorption and elution using a separation medium of Example 4.
Figure 8:
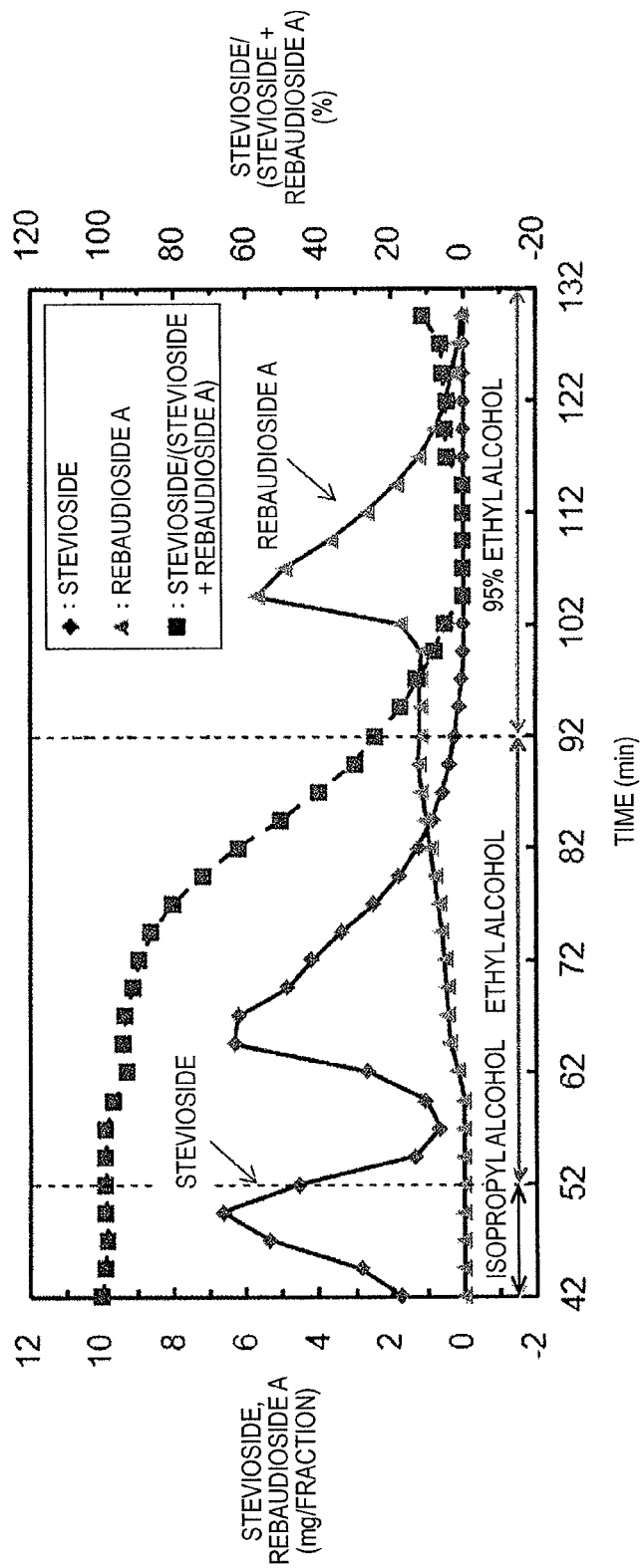
FIG. 8 is a graph illustrating contents of respective components and a ratio thereof as the results of performing evaluation of a separation property by adsorption and elution using the separation medium of Example 4.

FIG. 7 shows the adsorption and elution profile, and FIG. 8 shows the contents of stevioside and rebaudioside A in each fraction and (stevioside content)/(stevioside content+rebaudioside A content) (%).

In the fraction resulting from combining a part of fractions at the time of passing of an aqueous ethyl alcohol solution, the stevioside content was 35.7 mg, the rebaudioside A content was 7.3 mg, and (stevioside content)/(stevioside content+rebaudioside A content)=83%.

Furthermore, in the fraction resulting from combining a part of fractions at the time of passing of an aqueous 95% ethyl alcohol solution, the stevioside content was 0.80 mg, the rebaudioside A content was 29.4 mg, and (stevioside content)/(stevioside content+rebaudioside A content)=3%.

Furthermore, with respect to the coloring components in the solution containing steviol glycoside passed through the column packed with the separation medium, the value obtained by dividing the value measured with UV-VIS spectrometer at a wavelength of 420 nm and an optical path length of 1 cm by the total concentration of stevioside and rebaudioside A was 0.169 AU/(mg/mL)), but the value was reduced to 0.004 AU/(mg/mL) in the fraction containing stevioside and to 0.008 AU/(mg/mL) in the rebaudioside A fraction, and thus, separation of steviol glycosides and decolorization could be performed at the same time.

(Separation Property Evaluation 3 by Adsorption and Elution)

As the solution containing steviol glycoside used in the separation property evaluation 3 by adsorption and elution, the same solution as in the separation property evaluation 2 by adsorption and elution was used.

Separation Medium 5 obtained in Example 5 was packed into a polycarbonate-made column having an inner diameter of 9 mm and a length of 100 mm. The column was connected to a high-performance liquid chromatograph, and an isopropyl alcohol solution of steviol glycosides (stevioside concentration: 3.46 g/L, rebaudioside A concentration: 2.22 g/L, stevioside/rebaudioside A=61/39, the value, as indicator of coloring components in the solution, obtained by dividing the value measured with UV-VIS spectrometer at a wavelength of 420 nm and an optical path length of 1 cm by the total concentration of stevioside and rebaudioside A: 0.169 AU/(mg/mL)) was passed through the column at a flow velocity of 0.63 mL/min for 20 minutes (stevioside supply amount: 54.8 mg, rebaudioside A supply amount: 16.5 mg).

Subsequently, isopropyl alcohol was passed at a flow velocity of 0.63 mL/min for 10 minutes, an aqueous ethyl alcohol solution was then passed at a flow velocity of 0.63 mL/min for 20 minutes, an aqueous 95% ethyl alcohol solution was passed at a flow velocity of 0.63 mL/min for 30 minutes, and an aqueous 90% ethyl alcohol solution was passed at a flow velocity of 0.63 mL/min for 40 minutes.

In the process above, fractions were collected every 2.5 minutes, and the contents of stevioside and rebaudioside A were determined by high-performance liquid chromatograph analysis.

Figure 9:
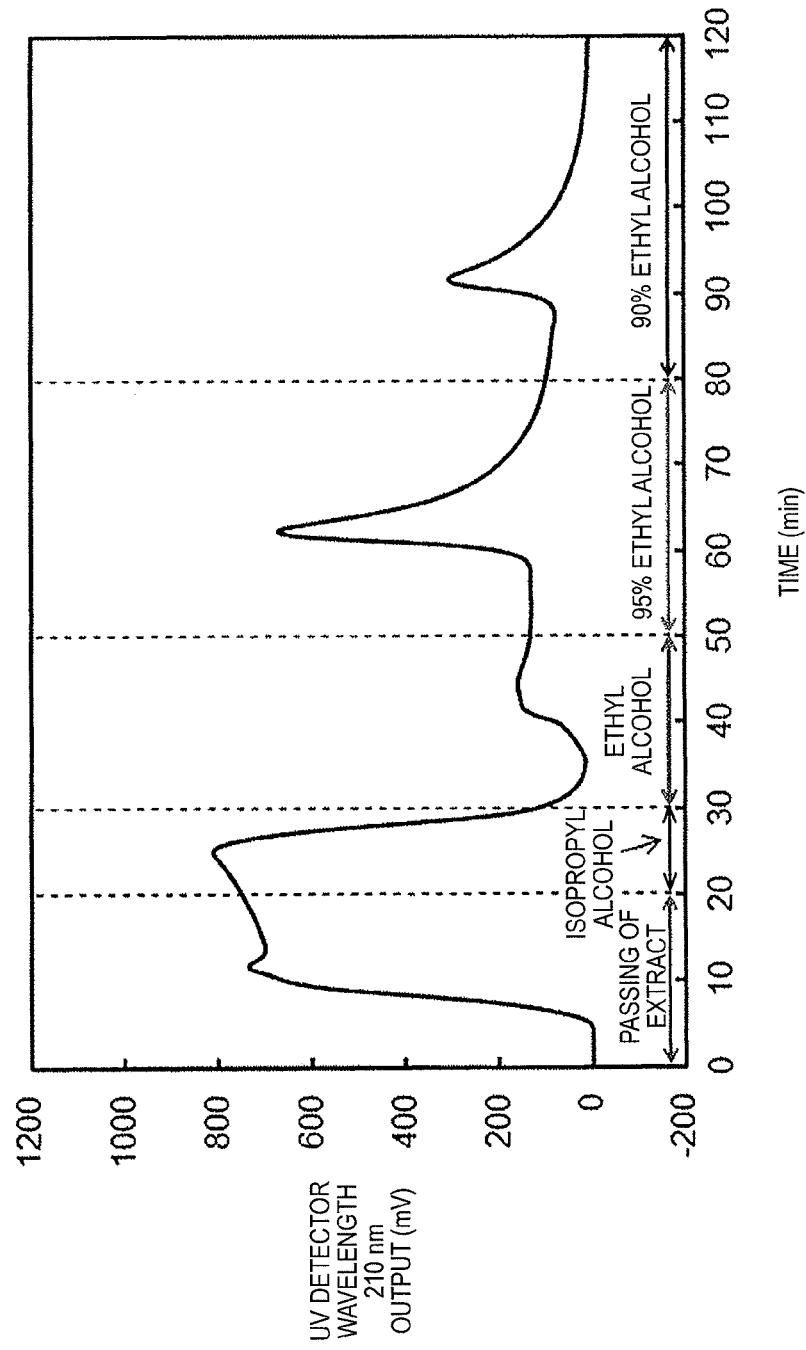
FIG. 9 is an adsorption and elution profile illustrating results of performing evaluation of a separation property by adsorption and elution using a separation medium of Example 5.
Figure 10:
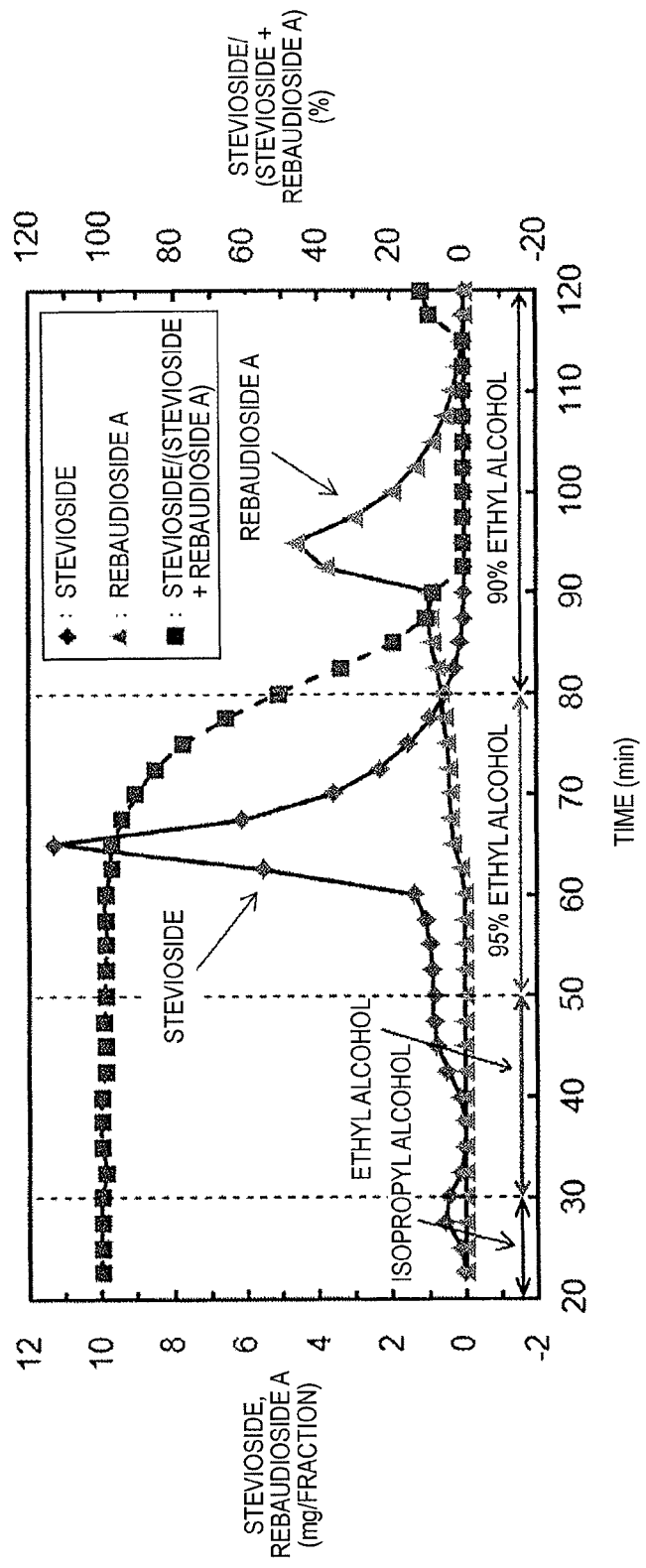
FIG. 10 is a graph illustrating contents of respective components and a ratio thereof as results of performing evaluation of a separation property by adsorption and elution using the separation medium of Example 5.

FIG. 9 shows the adsorption and elution profile, and FIG. 10 shows the contents of stevioside and rebaudioside A in each fraction and (stevioside content)/(stevioside content+rebaudioside A content) (%).

In the case of using Separation Medium 5 obtained in Example 5, elution of steviol glycosides at the time of passing of ethyl alcohol, which was observed in the separation property evaluation 2 by adsorption and elution (in the case of using Separation Medium 4), did not occur. In the fraction resulting from combining a part of fractions at the time of passing of an aqueous 95% ethyl alcohol solution, the stevioside content was 34.8 mg, the rebaudioside A content was 2.2 mg, and (stevioside content)/(stevioside content+rebaudioside A content)=97%.

Furthermore, in the fraction resulting from combining a part of fractions at the time of passing of an aqueous 90% ethyl alcohol solution, the stevioside content was 0.1 mg, the rebaudioside A content was 19.4 mg, and (stevioside content)/(stevioside content+rebaudioside A content)=1%.

Furthermore, with respect to the coloring components in the solution containing steviol glycoside passed through the column packed with the separation medium, the value obtained by dividing the value measured with UV-VIS spectrometer at a wavelength of 420 nm and an optical path length of 1 cm by the total concentration of stevioside and rebaudioside A was 0.169 AU/(mg/mL)), but the value was reduced to 0.003 AU/(mg/mL) in the stevioside-containing fraction and to 0.004 AU/(mg/mL) in the rebaudioside A fraction, and thus, separation of steviol glycosides and decolorization could be performed at the same time.

(Separation Property Evaluation 4 by Adsorption and Elution)

The solution containing steviol glycoside used in the separation property evaluation 4 by adsorption and elution was obtained using reagent stevioside and reagent rebaudioside A (produced by Tokyo Chemical Industry Co., Ltd.) and used in the form of an ethanol solution.

Separation Medium 6 obtained in Example 6 was packed into a polycarbonate-made column having an inner diameter of 18 mm and a length of 200 mm. The column was connected to a high-performance liquid chromatograph, and an ethanol solution of steviol glycosides (stevioside concentration: 1.14 g/L, rebaudioside A concentration: 2.57 g/L, stevioside/rebaudioside A=31/69) was passed through the column at a flow velocity of 2.54 mL/min for 30 minutes (stevioside supply amount: 86.5 mg, rebaudioside A supply amount: 195.3 mg).

Subsequently, ethyl alcohol was passed at a flow velocity of 2.54 mL/min for 20 minutes, an aqueous 97.5% ethyl alcohol solution was then passed at a flow velocity of 2.54 mL/min for 60 minutes, and an aqueous 90% ethyl alcohol solution was passed at a flow velocity of 2.54 mL/min for 60 minutes.

In the process above, fractions were collected every 3 minutes, and the contents of stevioside and rebaudioside A were determined by high-performance liquid chromatograph analysis.

Figure 11:
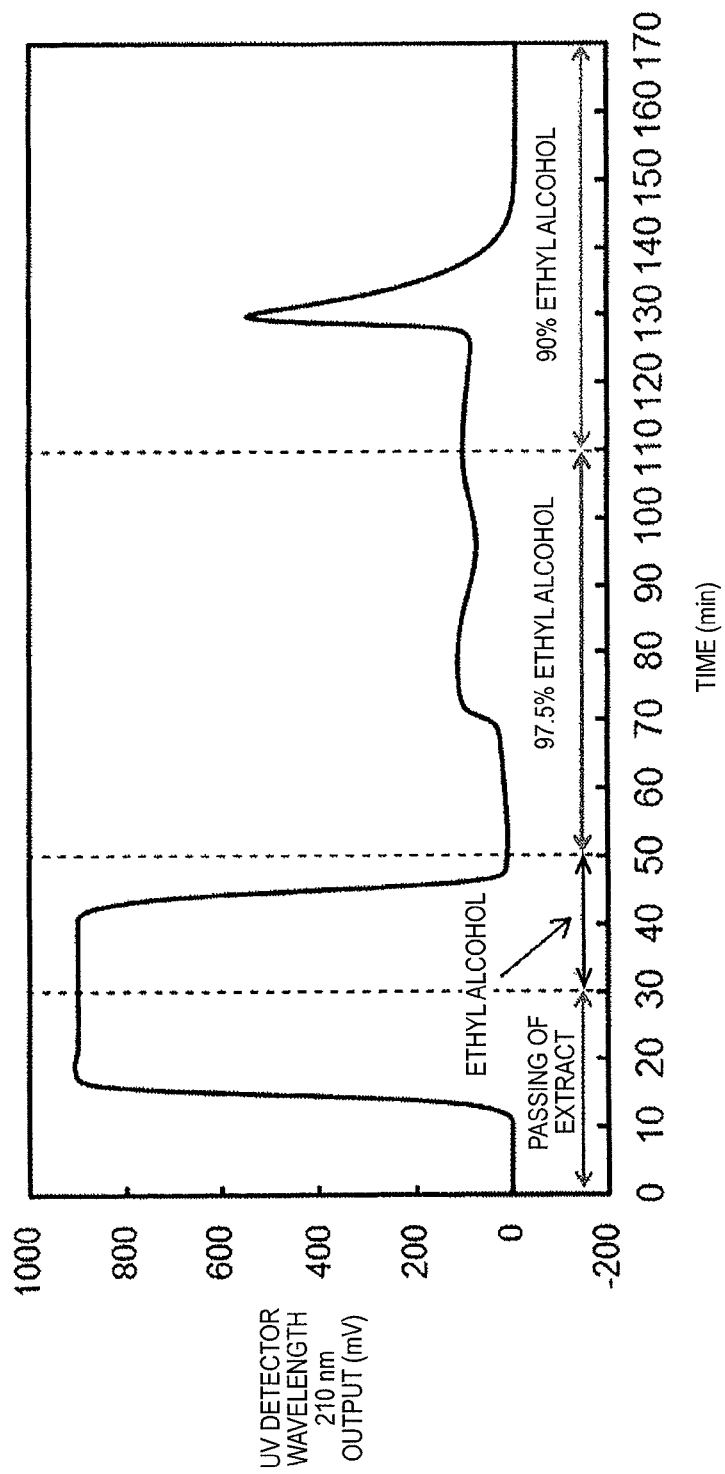
FIG. 11 is an adsorption and elution profile illustrating results of performing evaluation of a separation property by adsorption and elution using a separation medium of Example 6.
Figure 12:
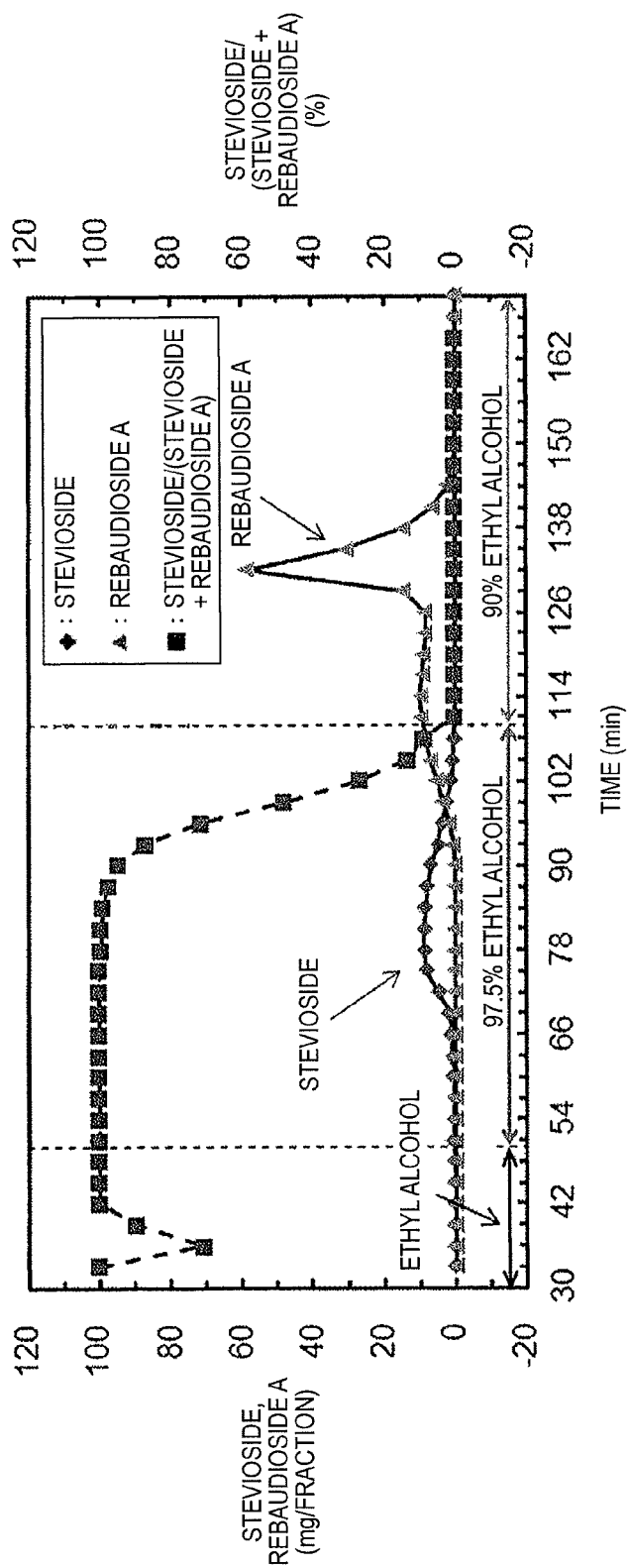
FIG. 12 is a graph illustrating contents of respective components and a ratio thereof as results of performing evaluation of a separation property by adsorption and elution using the separation medium of Example 6.

FIG. 11 shows the adsorption and elution profile, and FIG. 12 shows the contents of stevioside and rebaudioside A in each fraction and (stevioside content)/(stevioside content+rebaudioside A content) (%).

In the fraction resulting from combining a part of fractions at the time of passing of an aqueous 97.5% ethyl alcohol solution, the stevioside content was 59.1 mg, the rebaudioside A content was 0.6 mg, and (stevioside content)/(stevioside content+rebaudioside A content)=99%.

Furthermore, in the fraction resulting from combining a part of fractions at the time of passing of an aqueous 90% ethyl alcohol solution, the stevioside content was 0.8 mg, the rebaudioside A content was 196.0 mg, and (stevioside content)/(stevioside content+rebaudioside A content)=1%. In this connection, the content of rebaudioside A is larger than the supply amount, and this is presumed to be attributable to errors in the quantitative concentration at the high-performance liquid chromatograph analysis of fractions.

While the invention has been described in detail and with reference to specific embodiments thereof, it will be apparent to one skilled in the art that various changes and modifications can be made therein without departing from the spirit and scope of the invention. This application is based on Japanese Patent Application (Patent Application No. 2017-031392) filed on Feb. 22, 2017, the entirety of which is incorporated herein by way of reference. Furthermore, all references cited herein are incorporated in their entirety.

INDUSTRIAL APPLICABILITY

The separation medium of the present invention exhibits the adsorption and separation performance with high selectivity for steviol glycosides, particularly, for rebaudioside A, and allows decolorization of color components in the stevia leaf extract to be performed at the same time, and its practical value in the food industry field is significantly high.

The invention claimed is:

1. A separation method for steviol glycosides, comprising:
    loading a solution including two or more types of steviol glycosides to a separation medium; and
    allowing a solvent A to flow through the separation medium such that at least two types of steviol glycosides in the steviol glycosides are separated,
    wherein the separation medium comprises polyethyleneimine immobilized to porous particles of a (meth)acrylic polymer having a crosslinked structure, a diol structure, and a hydroxyl group.

2. The separation method for steviol glycosides according to claim 1, wherein the solution includes rebaudioside A such that at least one fraction is a fraction including the rebaudioside A as a main component.

3. The separation method for steviol glycosides according to claim 1, wherein the solvent A comprises alcohols freely miscible with water.

4. The separation method for steviol glycosides according to claim 1, further comprising:
    conducting a decolorization of a pigment component in the solution.

5. A separation method for steviol glycosides, comprising:
    separating at least two types of steviol glycosides in two or more types of steviol glycosides by using a separation medium,
    wherein the separation medium includes a diol structure and polyethyleneimine immobilized to porous particles of a (meth)acrylic polymer.

6. The separation method for steviol glycosides according to claim 5, wherein a mass average molecular weight of the polyethyleneimine is 200 or more.

7. The separation method for steviol glycosides according to claim 5, wherein a nitrogen content rate of the separation medium is in a range of from 0.3 to 30% by mass.

8. The separation method for steviol glycosides according to claim 5, wherein a pore diameter of the porous particles is in a range of from 1 to 1,000 nm.

9. The separation method for steviol glycosides according to claim 5, wherein the (meth)acrylic polymer has a crosslinked structure and a hydroxyl group.

10. A production method for steviol glycosides, comprising:
    the separation method of claim 5.

11. The separation method for steviol glycosides according to claim 2, wherein the solvent A comprises alcohols freely miscible with water.

12. The separation method for steviol glycosides according to claim 2, further comprising:
    conducting a decolorization of a pigment component in the solution.

13. The separation method for steviol glycosides according to claim 3, further comprising:
    conducting a decolorization of a pigment component in the solution.

14. The separation method for steviol glycosides according to claim 6, wherein a nitrogen content rate of the separation medium is in a range of from 0.3 to 30% by mass.

15. The separation method for steviol glycosides according to claim 6, wherein a pore diameter of the porous particles is in a range of from 1 to 1,000 nm.

16. The separation method for steviol glycosides according to claim 6, wherein the (meth)acrylic polymer has a crosslinked structure and a hydroxyl group.

17. A production method for steviol glycosides, comprising:
    the separation method of claim 6.

18. The separation method for steviol glycosides according to claim 7, wherein a pore diameter of the porous particles is in a range of from 1 to 1,000 nm.

19. The separation method for steviol glycosides according to claim 7, wherein the (meth)acrylic polymer has a crosslinked structure and a hydroxyl group.

20. A production method for steviol glycosides, comprising:
    the separation method of claim 7.

* * * * *